(12) United States Patent
Munoz et al.

(10) Patent No.: US 11,248,010 B2
(45) Date of Patent: *Feb. 15, 2022

(54) COMPOUNDS, COMPOSITIONS, AND METHODS FOR MODULATING CFTR

(71) Applicant: Proteostasis Therapeutics, Inc., Boston, MA (US)

(72) Inventors: Benito Munoz, Newtonville, MA (US); Daniel Parks, Pepperell, MA (US); Cecilia M. Bastos, South Grafton, MA (US)

(73) Assignee: Proteostasis Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,345

(22) Filed: Apr. 14, 2020

(65) Prior Publication Data

US 2021/0061823 A1  Mar. 4, 2021

Related U.S. Application Data

(63) Continuation of application No. 16/091,401, filed as application No. PCT/US2017/026579 on Apr. 7, 2017, now Pat. No. 10,662,207.

(60) Provisional application No. 62/319,439, filed on Apr. 7, 2016.

(51) Int. Cl.
| | | |
|---|---|---|
| *C07D 215/56* | (2006.01) | |
| *A61K 31/695* | (2006.01) | |
| *A61K 45/06* | (2006.01) | |
| *C07F 7/08* | (2006.01) | |

(52) U.S. Cl.
CPC .......... *C07F 7/0812* (2013.01); *A61K 31/695* (2013.01); *A61K 45/06* (2013.01); *C07D 215/56* (2013.01)

(58) Field of Classification Search
CPC ..... C07F 7/0812; A61K 31/695; A61K 45/06; C07D 215/56
See application file for complete search history.

(56) References Cited

U.S. PATENT DOCUMENTS

| | | | |
|---|---|---|---|
| 5,780,393 A | 7/1998 | Newton | |
| 5,888,941 A | 3/1999 | Bartroli et al. | |
| 7,846,951 B2 | 12/2010 | Miller et al. | |
| 7,915,297 B2 | 3/2011 | Cho et al. | |
| 7,981,935 B2 | 7/2011 | Olson et al. | |
| 8,193,225 B2 | 6/2012 | Schneider et al. | |
| 8,236,838 B2 | 8/2012 | Jones et al. | |
| 8,623,860 B2 | 1/2014 | Fleck et al. | |
| 8,815,924 B2 | 8/2014 | Dorsch et al. | |
| 9,745,292 B2 | 8/2017 | Bastos et al. | |
| 9,790,219 B2 | 10/2017 | Bastos et al. | |
| 10,017,503 B2 | 7/2018 | Bastos et al. | |
| 10,174,014 B2 | 1/2019 | Bastos et al. | |
| 10,344,023 B2 | 7/2019 | Bastos et al. | |
| 10,392,372 B2 | 8/2019 | Bastos et al. | |
| 10,392,378 B2 | 8/2019 | Bastos et al. | |
| 10,548,878 B2 | 2/2020 | Munoz et al. | |
| 10,550,106 B2 | 2/2020 | Munoz et al. | |
| 10,662,207 B2 * | 5/2020 | Munoz | A61K 45/06 |
| 2006/0041006 A1 | 2/2006 | Ibrahim et al. | |
| 2006/0100226 A1 | 5/2006 | Sikorski et al. | |
| 2008/0090882 A1 | 4/2008 | Dorsch et al. | |
| 2009/0069288 A1 | 3/2009 | Breinlinger et al. | |
| 2009/0163545 A1 | 6/2009 | Goldfarb | |
| 2009/0264486 A1 | 10/2009 | Jones et al. | |
| 2009/0318429 A1 | 12/2009 | Doyle et al. | |
| 2010/0234367 A1 | 9/2010 | Nomura et al. | |
| 2011/0003784 A1 | 1/2011 | Garvey et al. | |
| 2011/0082181 A1 | 4/2011 | Seiders et al. | |
| 2011/0212975 A1 | 9/2011 | Kao et al. | |
| 2012/0095002 A1 | 4/2012 | Ratcliffe et al. | |
| 2012/0264738 A1 | 10/2012 | Sugimoto et al. | |
| 2013/0217883 A1 | 8/2013 | Adaway | |
| 2013/0237502 A1 | 9/2013 | Curtis et al. | |
| 2014/0073667 A1 | 3/2014 | Morgan | |
| 2014/0364467 A1 | 12/2014 | Schneider et al. | |
| 2016/0151335 A1 | 6/2016 | Tait et al. | |
| 2017/0001991 A1 | 1/2017 | Bastos et al. | |
| 2017/0001993 A1 | 1/2017 | Bastos et al. | |
| 2017/0233379 A1 | 8/2017 | Bastos et al. | |
| 2017/0362214 A1 | 12/2017 | Bastos et al. | |
| 2017/0369480 A1 | 12/2017 | Bastos et al. | |
| 2017/0369482 A1 | 12/2017 | Bastos et al. | |
| 2018/0127400 A1 | 5/2018 | Bastos et al. | |
| 2018/0147187 A1 | 5/2018 | Bastos et al. | |
| 2018/0214419 A1 | 8/2018 | Munoz et al. | |
| 2018/0291006 A1 | 10/2018 | Munoz et al. | |

(Continued)

FOREIGN PATENT DOCUMENTS

| | | | |
|---|---|---|---|
| CA | 2736441 A1 | 10/2012 | |
| EP | 0337263 A2 | 10/1989 | |

(Continued)

OTHER PUBLICATIONS

U.S. Appl. No. 16/872,883, Methods of Modulating CFTR Activity, filed May 12, 2020.

U.S. Pat. No. 9,790,219, issued on Oct. 17, 2017, U.S. Appl. No. 15/125,827; published as US 2017/0001993 on Jan. 5, 2017, Compounds, Compositions, and Methods for Increasing CFTR Activity, filed Sep. 13, 2016.

U.S. Pat. No. 9,745,292, issued on Aug. 29, 2017, U.S. Appl. No. 15/125,830; published as US 2017/0001991 on Jan. 5, 2017, Compounds, Compositions, and Methods for Increasing CFTR Activity, filed Sep. 13, 2016.

U.S. Pat. No. 10,017,503, issued on Jul. 10, 2018; U.S. Appl. No. 15/653,934, published as US 2018/0127400 on May 10, 2018, Compounds, Compositions, and Methods for Increasing CFTR Activity, filed Jul. 19, 2017.

(Continued)

*Primary Examiner* — Timothy R Rozof
(74) *Attorney, Agent, or Firm* — Goodwin Procter LLP

(57) ABSTRACT

The present disclosure is directed to disclosed compounds that modulate e.g., address underlying defects in cellular processing of CFTR activity.

11 Claims, No Drawings

(56) References Cited

U.S. PATENT DOCUMENTS

| | | | |
|---|---|---|---|
| 2018/0327363 | A1 | 11/2018 | Bastos et al. |
| 2018/0369209 | A1 | 12/2018 | Miller et al. |
| 2019/0022071 | A1 | 1/2019 | Lee |
| 2019/0153000 | A1 | 5/2019 | Munoz et al. |
| 2019/0154661 | A1 | 5/2019 | Miller et al. |
| 2019/0308960 | A1 | 10/2019 | Bastos et al. |
| 2020/0010461 | A1 | 1/2020 | Parks et al. |

FOREIGN PATENT DOCUMENTS

| | | |
|---|---|---|
| EP | 0957099 A2 | 11/1999 |
| JP | 2006176443 A | 7/2006 |
| JP | 2007086584 A | 4/2007 |
| WO | WO-2002000651 A2 | 1/2002 |
| WO | WO-2003093297 A2 | 11/2003 |
| WO | WO-2005035514 A2 | 4/2005 |
| WO | WO-2005077345 A1 | 8/2005 |
| WO | WO-2005077373 A2 | 8/2005 |
| WO | WO-2006014134 A1 | 2/2006 |
| WO | WO-2006136924 A1 | 12/2006 |
| WO | WO-2007075896 A2 | 7/2007 |
| WO | WO-2007078113 A1 | 7/2007 |
| WO | WO-2007086584 A1 | 8/2007 |
| WO | WO-2007126362 A1 | 11/2007 |
| WO | WO-2008046072 A2 | 4/2008 |
| WO | WO-2008/051757 A1 | 5/2008 |
| WO | WO-2008070739 A1 | 6/2008 |
| WO | WO-2009005269 A2 | 1/2009 |
| WO | WO-2009011850 A2 | 1/2009 |
| WO | WO-2009016241 A1 | 2/2009 |
| WO | WO-2010089297 A1 | 8/2010 |
| WO | WO-2010142801 A1 | 12/2010 |
| WO | WO-2011008931 A2 | 1/2011 |
| WO | WO-2011133953 A1 | 10/2011 |
| WO | WO-2012007500 A2 | 1/2012 |
| WO | WO-2012158885 A1 | 11/2012 |
| WO | WO-2013019561 A1 | 2/2013 |
| WO | WO-2013146970 A1 | 10/2013 |
| WO | WO-2014144860 A1 | 9/2014 |
| WO | WO-2014181287 A1 | 11/2014 |
| WO | WO-2014210159 A1 | 12/2014 |
| WO | WO-2015051230 A1 | 4/2015 |
| WO | WO-2015138909 A1 | 9/2015 |
| WO | WO-2015138934 A1 | 9/2015 |
| WO | WO-2015196071 A1 | 12/2015 |
| WO | WO-2016054560 A1 | 4/2016 |
| WO | WO-2016105468 A1 | 6/2016 |
| WO | WO-2016105477 A1 | 6/2016 |
| WO | WO-2016105484 A1 | 6/2016 |
| WO | WO-2016105485 A2 | 6/2016 |
| WO | WO-2016115090 A1 | 7/2016 |
| WO | WO-2017019589 A1 | 2/2017 |
| WO | WO-2017062581 A1 | 4/2017 |
| WO | WO-2017112853 A1 | 6/2017 |

OTHER PUBLICATIONS

U.S. Pat. No. 10,174,014, issued on Jan. 8, 2019; U.S. Appl. No. 15/320,172, published as US 2017/0233379 on Aug. 17, 2017, Compounds, Compositions, and Methods for Increasing CFTR Activity, filed Dec. 19, 2016.

U.S. Pat. No. 10,738,040 issued on Aug. 11, 2020; U.S. Appl. No. 16/190,964 published as US-2019/0308960 on Oct. 10, 2019, Compounds, Compositions, and Methods for Increasing CFTR Activity, filed Nov. 14, 2018.

U.S. Appl. No. 16/913,824, Compounds, Compositions, and Methods for Increasing CFTR Activity, filed Jun. 26, 2020.

U.S. Pat. No. 10,392,372, issued on Aug. 27, 2019; U.S. Appl. No. 15/539,392, published as US 2017/0369480 on Dec. 28, 2017, Compounds, Compositions, and Methods for Increasing CFTR Activity, filed Jun. 23, 2017.

U.S. Appl. No. 16/510,406, published as US 2020/0190072 on Jun. 18, 2020, Compounds, Compositions, and Methods for Increasing CFTR Activity, filed Jul. 12, 2019.

U.S. Pat. No. 10,392,378; issued on Aug. 27, 2019; U.S. Appl. No. 15/539,397, published as US 2017/0369482 on Dec. 28, 2017, Derivatives of 5-Phenyl- or 5-Heteroarylathiazol-2-Carboxylic Amide Useful for the Treatment of Inter Alia Cystic Fibrosis, filed Jun. 23, 2017.

U.S. Pat. No. 10,738,011 issued on Aug. 11, 2020; U.S. Appl. No. 15/539,401, published as US 2018/0327363 on Nov. 15, 2018, Derivatives of 5-(Hetero)Arylpyrazol-3-Carboxylic Amide or 1-(Hetero)Aryltriazol-4-Carboxylic Amide Useful for the Treatment of Inter Alia Cystic Fibrosis, filed Jun. 23, 2017.

U.S. Appl. No. 16/916,267, Derivatives of 5-(Hetero)Arylpyrazol-3-Carboxylic Amide or 1-(Hetero)Aryltriazol-4-Carboxylic Amide Useful for the Treatment of Inter Alia Cystic Fibrosis, filed Jun. 30, 2020.

U.S. Pat. No. 10,344,023; issued on Jul. 9, 2019; U.S. Appl. No. 15/539,405, published as US 2017/0362214 on Dec. 21, 2017, Derivatives of 3-Heteroarylisoxazol-5-Carboxylic Amide Useful for the Treatment of Inter Alia Cystic Fibrosis, filed Jun. 23, 2017.

U.S. Pat. No. 10,548,878; issued on Feb. 4, 2020; U.S. Appl. No. 15/747,290, published as US 2018/0214419 on Aug. 2, 2018, Compounds, Compositions, and Methods of Increasing CFTR Activity, filed Jan. 24, 2018.

U.S. Appl. No. 16/710,688, Compounds, Compositions, and Methods of Increasing CFTR Activity, filed Dec. 11, 2019.

U.S. Pat. No. 10,550,106; issued on Feb. 4, 2020; U.S. Appl. No. 15/766,667, published as US 2018/0291006 on Oct. 11, 2018, Compounds, Compositions, and Methods for Modulating CFTR, filed Apr. 6, 2018.

U.S. Appl. No. 16/716,765, Compounds, Compositions, and Methods for Modulating CFTR, filed Dec. 17, 2019.

U.S. Appl. No. 16/065,384, published as US 2018/0369209 on Dec. 27, 2018, Methods of Treating Pulmonary Diseases and Disorders, filed Jun. 22, 2018.

U.S. Pat. No. 10,662,207; issued on May 26, 2020; U.S. Appl. No. 16/091,401, published as US 2019/0153000 on May 23, 2019, Compounds, Compositions, and Methods for Modulating CFTR, filed Oct. 4, 2018.

U.S. Appl. No. 16/848,345, Compounds, Compositions, and Methods for Modulating CFTR, filed Apr. 14, 2020.

U.S. Appl. No. 16/300,219; published as US 2019/0154661 on May 23, 2019, Methods of Identifying CFTR Modulators, filed Nov. 9, 2018.

U.S. Appl. No. 16/311,397; published as US 2020/0010461 on Jan. 9, 2020, Compounds, Compositions, and Methods for Increasing CFTR Activity, filed Dec. 19, 2018.

U.S. Appl. No. 16/345,081, published as US 2019/0248779 on Aug. 15, 2019, Compounds, Compositions, and Methods for Increasing CFTR Activity, filed Apr. 25, 2019.

U.S. Appl. No. 16/345,084, published as US 2019/0248765 on Aug. 15, 2019, Compounds, Compositions, and Methods for Increasing CFTR Activity, filed Apr. 25, 2019.

U.S. Appl. No. 16/609,076, published on US 2020/0055844 on Feb. 20, 2020, 4-Sulfonylaminocarbonylquinoline Derivatives for Increasing CFTR Activity, filed Oct. 28, 2019.

U.S. Appl. No. 16/753,826, Compounds, Compositions, and Methods for Increasing CFTR Activity, filed Apr. 6, 2020.

U.S. Appl. No. 16/958,899, Methods of Quantifying CFTR Protein Expression, filed Jun. 29, 2020.

"AID 775-Screen for Chemicals that Extend Yeast Lifespan," PubChem, 1-11 (Jul. 12, 2007), XP055331102.

Bai et al., "Synthesis and Structure-Activity Relationship Studies of Conformationally Flexible Tetrahydroisoquinolinyl Triazole Carboxamide and Triazole Substituted Benzamide Analogues as sigma 2 Receptor Ligands," Journal of Medicinal Chemistry, 57:10 4239-4251(2014), XP002754990.

CAS Registry No. 797781-85-2 (available Dec. 15, 2004).

Chang, X., "3-(2-chlorophenyl)-N-methylisoxazole-5-Carboxamide," ACTA Crystallographica, Section E: Structure Reports Online, vol. E63(7), pp. 03074-sup-7 (2007).

Compound Summary for CID 70741394, Pubchem: Create Date: Mar. 4, 2013 [retrieved on May 12, 2015].

(56) References Cited

OTHER PUBLICATIONS

Compound Summary for CID 70756362, Pubchem: Create Date: Mar. 4, 2013 [retrieved on May 12, 2015].
Compound Summary for: CID 36257620, Pubchem: Create Date: May 29, 2009 [retrieved on May 12, 2015].
Compound Summary for: CID 55795703, Pubchem: Create Date: Jan. 25, 2012 [retrieved on May 12, 2015].
Demina et al., "5-substituted Pyridylisoxazoles as Effective Inhibitors of Platelet Aggregation," Russian Chemical Bulletin, International Edition, vol. 63(2) 2095-2113 (2014).
International Search Report and Written Opinion for International Application No. PCT/US2014/044100, dated Oct. 10, 2014, 8 pages.
International Search Report and Written Opinion for International Application No. PCT/US2015/000189, dated Mar. 18, 2016, 10 pages.
International Search Report and Written Opinion for International Application No. PCT/US2015/000202, dated Mar. 22, 2016, 8 pages.
International Search Report and Written Opinion for International Application No. PCT/US2015/000211, dated Mar. 29, 2016, 10 pages.
International Search Report and Written Opinion for International Application No. PCT/US2015/000212, dated Jul. 1, 2016, 22 pages.
International Search Report and Written Opinion for International Application No. PCT/US2015/020460, dated Jun. 9, 2015, 7 pages.
International Search Report and Written Opinion for International Application No. PCT/US2015/020499, dated Jun. 9, 2015, 8 pages.
International Search Report and Written Opinion for International Application No. PCT/US2015/036691, dated Aug. 20, 2015, 12 pages.
International Search Report and Written Opinion for International Application No. PCT/US2016/012982, dated Mar. 7, 2016, 12 pages.
International Search Report and Written Opinion for International Application No. PCT/US2016/043835, dated Oct. 10, 2016, 8 pages.
International Search Report and Written Opinion for International Application No. PCT/US2016/068266, dated Feb. 27, 2017, 11 pages.
International Search Report and Written Opinion for International Application No. PCT/US2017/026579, dated Jun. 6, 2017, 9 pgs.
International Search report and Written Opinion for International Application No. PCT/US2017/040606, dated Nov. 30, 2016, 10 pages.
Kalid et al., "Small Molecule Correctors of F508del-CFTR Discovered by Structure-based Virtual Screening," Journal of Computer-Aided Molecular Design, vol. 24:971-991 (2010).
Lack et al., "Targeting the Binding Function 3 (BF3) Site of the Human Androgen Receptor through Virtual Screening," Journal of Medicinal Chemistry, vol. 54(24) 8563-8573 (2011).

Liedtke, W., "Role of TRPV ion Channels in Sensory Transduction of Osmotic Stimuli in Mammals," Experimental Physiology, 92:3 507-512 (2007) XP055252392.
Lukevics et al.,"Synthesis and Cytotoxicity of Silyl- and Carbonyl-substituted Isoxazoles," Chemistry of Heterocyclic Compounds, Springer New York LLC, vol. 36(10); 1226-1231 (1995).
Munchhof et al., "Discovery of PF-04449913, a Potent and Orally Bioavailable Inhibitor of Smoothened," ACS Medicinal Chemistry Letters, vol. 3(2) 106-111 (2012).
Phuan Puay-Wah et al., "Potentiators of Defective Delta F508-CFTR Gating that Do Not Interfere with Corrector Action," XP002754658, Database Accession No. PREV201500722877, Database Biosis [Online] Biosciences Information Service, Philadelphia, PA, US; Oct. 1, 2015 (Oct. 1, 2015). 1 page.
Pubchem: "ST062658 | C15H12N2O3—PubChem", Jul. 9, 2005 (Jul. 9, 2005), XP055331105, Retrieved from the Internet: URL:https://pubchem.ncbi.nlm.nih.gov/compound/973870#section=Biological-Test-Results [retrieved on Dec. 22, 2016].
Qian et al., "Potent MCH-1 Receptor Antagonists from Cis-1,4-Diaminocyclohexane-derived Indane Analogs," Bioorganic & Medicinal Chemistry Letters, 23:14 4216-4220 (2013).
Showell et al., "Chemistry Challenges in Lead Optimization: Silicon Isosteres in Drug Discovery," Drug Discovery Today 8: 551-556 (2003).
Stoops et al., "Identification and Optimization of Small Molecules that Restore E-cadherin Expression and Reduce Invasion in Colorectal Carcinoma Cells," ACS Chemical Biology, American Chemical Society, Washington, DC, US, vol. 6., No. 5, pp. 452-465 (2011).
Supplemental European Search Report dated Jan. 9, 2017 in European Patent No. 14816975.8 (19 pages).
U.S. Appl. No. 15/542,997, "Compounds, Compositions, and Methods for Increasing CFTR Activity," filed Jul. 12, 2017 (175 pages).
U.S. Appl. No. 15/653,934, "Compounds, Compositions, and Methods for Increasing CFTR Activity," filed on Jul. 19, 2017 (76 pages).
U.S. Appl. No. 15/697,901, "Compounds, Compositions, and Methods for Increasing CFTR Activity," filed on Sep. 7, 2017 (112 pages).
U.S. Appl. No. 16/716,765, "Compounds, Compositions, and Methods for Modulating CFTR," filed on Dec. 17, 2019 (310 pages).
International Search Report and Written Opinion for International Application No. PCT/US2018/030123, dated Jul. 9, 2018, 10 pgs.
Davies, J. et al., "Efficacy and Safety of Ivacaftor in Patients Aged 6 to 11 Years with Cystic Fibrosis with G551D Mutation," American Journal of Respiratory and Critical Care Medicine, vol. 187, No. 11, pp. 1219-1225 (2013).
Franz, A. et al., "Organosilicon Molecules with Medicinal Applications," Journal of Medicinal Chemistry, vol. 56, No. 2, pp. 388-405 (2012).
Heinonen, P. et al., "Synthesis and Pharmacological Properties of 4 (5)-(2-ethyl-2-hydroxy-2 silainden-yl) Imidazole, a Silicon Analogue of Atipamezole," European Journal of Medicinal Chemistry, vol. 31, No. 9, pp. 725-729 (1996).

* cited by examiner

COMPOUNDS, COMPOSITIONS, AND METHODS FOR MODULATING CFTR

CROSS REFERENCE TO RELATED APPLICATIONS

This application is a continuation of U.S. patent application Ser. No. 16/091,401, filed Oct. 4, 2018, which is a national stage filing under U.S.C. § 371 of PCT/US2017/026579, filed Apr. 7, 2017, which claims the benefit of, and priority to, U.S. provisional application No. 62/319,439, filed Apr. 7, 2016; the content of each of which is hereby incorporated by reference herein in its entirety.

BACKGROUND

Cells normally maintain a balance between protein synthesis, folding, trafficking, aggregation, and degradation, referred to as protein homeostasis, utilizing sensors and networks of pathways (Sitia et al., *Nature* 426: 891-894, 2003; Ron et al., *Nat Rev Mol Cell Biol* 8: 519-529, 2007). The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation (Wiseman et al., *Cell* 131: 809-821, 2007). Whether a given protein folds in a certain cell type depends on the distribution, concentration, and subcellular localization of chaperones, folding enzymes, metabolites and the like (Wiseman et al.). Cystic fibrosis and other maladies of protein misfolding arise as a result of an imbalance in the capacity of the protein homeostasis (proteostasis) environment to handle the reduced energetic stability of misfolded, mutated proteins that are critical for normal physiology (Balch et al., *Science* 319, 916-9 (2008); Powers, et al., *Annu Rev Biochem* 78, 959-91 (2009); Hutt et al., *FEBS Lett* 583, 2639-46 (2009)).

Cystic Fibrosis (CF) is caused by mutations in the cystic fibrosis transmembrane conductance regulator (CFTR) gene which encodes a multi-membrane spanning epithelial chloride channel (Riordan et al., *Annu Rev Biochem* 77, 701-26 (2008)). Approximately ninety percent of patients have a deletion of phenylalanine (Phe) 508 ($\Delta$F508) on at least one allele. This mutation results in disruption of the energetics of the protein fold leading to degradation of CFTR in the endoplasmic reticulum (ER). The $\Delta$F508 mutation is thus associated with defective folding and trafficking, as well as enhanced degradation of the mutant CFTR protein (Qu et al., *J Biol Chem* 272, 15739-44 (1997)). The loss of a functional CFTR channel at the plasma membrane disrupts ionic homeostasis (Cl$^-$, Na$^+$, HCO$_3^-$) and airway surface hydration leading to reduced lung function (Riordan et al.). Reduced periciliary liquid volume and increased mucus viscosity impede mucociliary clearance resulting in chronic infection and inflammation, phenotypic hallmarks of CF disease (Boucher, *J Intern Med* 261, 5-16 (2007)). In addition to respiratory dysfunction, $\Delta$F508 CFTR also impacts the normal function of additional organs (pancreas, intestine, gall bladder), suggesting that the loss-of-function impacts multiple downstream pathways that will require correction.

In addition to cystic fibrosis, mutations in the CFTR gene and/or the activity of the CFTR channel has also been implicated in other conditions, including for example, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), dry eye disease, Sjogren's syndrome and chronic sinusitis, cholestatic liver disease (e.g. Primary biliary cirrhosis (PBC) and primary sclerosing cholangitis (PSC)) (Sloane et al. (2012), PLoS ONE 7(6): e39809.doi: 10.1371/journal. pone.0039809; Bombieri et al. (2011), J Cyst Fibros. 2011 June; 10 Suppl 2:S86-102; (Albert et al. (2008), Clinical Respiratory Medicine, Third Ed., Mosby Inc.; Levin et al. (2005), Invest Ophthalmol Vis Sci., 46(4): 1428-34; Froussard (2007), Pancreas 35(1): 94-5), Son et al. (2017) J Med Chem 60(6):2401-10.

A potential strategy for improving e.g., a drug's metabolic properties, efficacy, and/or safety profile is silicon modification. At the same time, because the general properties are similar to those of carbon, replacement of carbon by silicon would not be expected to affect e.g., the biochemical potency and/or selectivity of the drug as compared to the original chemical entity that contains only carbon.

There remains a need in the art for compounds, compositions and methods of increasing CFTR activity as well as for methods of treating CF, other CFTR-related diseases, and other maladies of protein misfolding.

SUMMARY

This disclosure is directed in part to a compound selected from N-(2,4-di-tert-butyl-5-hydroxyphenyl)-4-oxo-1,4-dihydroquinoline-3-carboxamide and a pharmaceutically acceptable salt thereof, wherein at least one carbon atom is replaced by silicon. In some embodiments, the carbon atom(s) replaced by silicon is a non-aromatic carbon. In other embodiments, the carbon atom(s) replaced by silicon is the quaternary carbon atom of one tert-butyl moiety or two tert-butyl moieties. In certain embodiments, one or more hydrogens are replaced by deuterium.

For example, disclosed herein are compounds having Formula I:

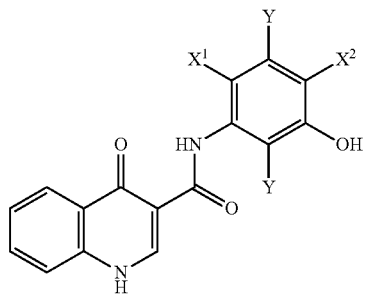

Formula I or a pharmaceutically acceptable salt thereof, in which $X^1$, $X^2$ and Y are as defined herein.

Also contemplated herein are pharmaceutical compositions that include a disclosed compound, e.g., N-(2,4-di-tert-butyl-5-hydroxyphenyl)-4-oxo-1,4-dihydroquinoline-3-carboxamide wherein at least one carbon atom is replaced by silicon, and a pharmaceutically acceptable carrier or excipient. Further contemplated herein are pharmaceutical compositions that include a disclosed compound such as those compounds having Formula I and a pharmaceutically acceptable carrier or excipient. In certain embodiments, the compositions can include at least one additional CFTR modulator, for example, may include one, two, three, four, five or more additional CFTR modulators.

In certain embodiments, a method is provided comprising administering a disclosed compound to a subject (e.g., a human patient) suffering from a disease associated with decreased CFTR activity (e.g., cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), chronic sinusitis, dry eye disease, protein C deficiency, A-β-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, Sjogren's syndrome, familial hypercholesterolemia, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, nephrogenic DI, Charcot-Marie Tooth syndrome, Perlizaeus-Merzbacher disease, Alzheimer's disease, Parkinson's disease, amyotrophic lateral sclerosis, progressive supranuclear palsy, Pick's disease, Huntington's disease, spinocerebellar ataxia type I, spinal and bulbar muscular atrophy, dentatorubral pallidoluysian, myotonic dystrophy, hereditary Creutzfeldt-Jakob disease (due to prion protein processing defect), Fabry disease, cholestatic liver disease (e.g. Primary biliary cirrhosis (PBC) and primary sclerosing cholangitis (PSC)), and Straussler-Scheinker syndrome). In certain embodiments, the disease is cystic fibrosis. For example, contemplated herein is a method for treating a patient suffering from cystic fibrosis comprising administering to said patient an effective amount of a disclosed compound.

In some embodiments, disclosed methods described herein can further include administering at least one additional CFTR modulator e.g., administering at least two, three, four or five additional CFTR modulators. In certain embodiments, at least one additional CFTR modulator is a CFTR corrector (e.g., VX-661 (tezacaftor), VX-152, VX-440, VX-445, VX-659, or VX-983) or, e.g., VX-809 (lumacaftor) or, e.g., GLPG2851, GLPG2665, GLPG2737, or GLPG2222.

DETAILED DESCRIPTION

As used herein, the words "a" and "an" are meant to include one or more unless otherwise specified. For example, the term "an agent" encompasses both a single agent and a combination of two or more agents.

As discussed above, the present disclosure is directed in part to compounds as described herein having the Formula I or a pharmaceutically acceptable salt thereof, pharmaceutical compositions, methods of increasing CFTR activity and methods of treating cystic fibrosis. In part, the disclosure relates to novel derivatives of ivacaftor, and pharmaceutically acceptable salts thereof. Ivacaftor, also known as VX-770 and by the chemical name, N-(2,4-di-tert-butyl-5-hydroxyphenyl)-4-oxo-1,4-dihydroquinoline-3-carboxamide, acts as a CFTR potentiator.

For example, provided herein is a compound selected from N-(2,4-di-tert-butyl-5-hydroxyphenyl)-4-oxo-1,4-dihydroquinoline-3-carboxamide and a pharmaceutically acceptable salt thereof, wherein at least one carbon atom may be replaced by silicon.

In certain embodiments, one carbon atom may be replaced by silicon. In other embodiments, two carbons atoms may be replaced by silicon. For example, the carbon replaced by silicon may be a non-aromatic carbon. In another embodiment, the quaternary carbon atom of one tert-butyl moiety may be replaced by silicon. In a further embodiment, the quaternary carbon atoms of two tert-butyl moieties may be replaced by silicon. In certain embodiments, one or more hydrogens may be replaced by deuterium. For example, one or more hydrogens of the tert-butyl moiety may be replaced by deuterium.

Also provided herein are compounds having Formula I:

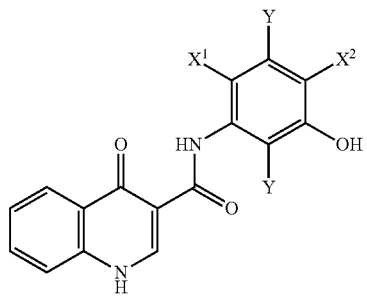

Formula I or a pharmaceutically acceptable salt thereof, wherein:

$X^1$ is selected from the group consisting of —Si($R^3$)$_3$, —C(CY$_3$)$_3$, hydrogen, halogen, $C_{1-3}$alkyl optionally substituted by one or more halogens, $C_{3-6}$cycloalkyl, and 4-6 membered saturated monocyclic heterocyclyl; wherein $C_{3-6}$cycloalkyl and 4-6 membered saturated monocyclic heterocyclyl may be optionally be substituted by one, two, three or more substituents each independently selected for each occurrence from $R^{11}$;

$X^2$ is selected from the group consisting of —Si($R^3$)$_3$ and —C(CY$_3$)$_3$;

wherein at least one of $X^1$ or $X^2$ is —Si($R^3$)$_3$;

$R^3$ is independently selected for each occurrence from the group consisting of hydroxyl, $C_{1-4}$alkyl, $C_{1-4}$alkoxy, and phenyl, wherein $C_{1-4}$alkyl, $C_{1-4}$alkoxy, and phenyl may optionally be substituted by one, two, three or more deuterium atoms; or two $R^3$ groups together with the silicon to which they are attached form a 4-6 membered saturated cyclosilane;

Y is independently selected for each occurrence from the group consisting of hydrogen and deuterium; and $R^{11}$ is independently selected for each occurrence from the group consisting of hydrogen, halogen, hydroxyl, cyano, and $C_{1-6}$alkyl; wherein $C_{1-6}$alkyl may be optionally substituted by one or more substituents each independently selected for each occurrence from the group consisting of halogen, hydroxyl, and $C_{1-6}$alkoxy.

In some embodiments, one of $X^1$ or $X^2$ is —C(CH$_3$)$_3$ and the other one of $X^1$ or $X^2$ is —Si($R^3$)$_3$.

For example, in certain embodiments the compound may be represented by:

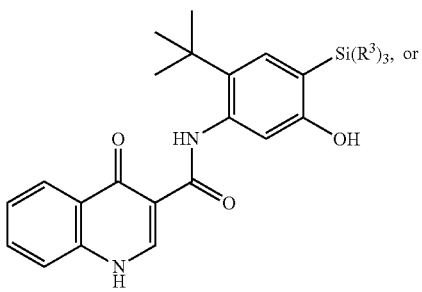
Ia

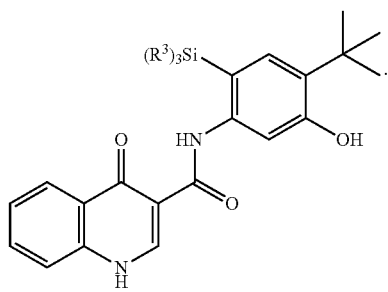
Ib

In other embodiments, both of X¹ and X² are —Si(R³)₃.

For example, in certain embodiments the compound may be represented by:

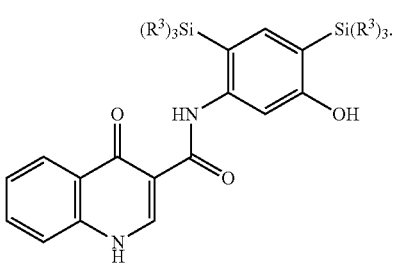
Ic

In some embodiments, R³ may be independently selected for each occurrence from the group consisting of hydroxyl, methyl, ethyl, isopropyl, tert-butyl, methoxy, ethoxy, isopropoxy, tert-butoxy, and phenyl, wherein methyl, ethyl, isopropyl, tert-butyl, methoxy, ethoxy, isopropoxy, tert-butoxy, and phenyl may optionally be substituted by one, two, three or more deuterium atoms. For example, R³ may be independently selected for each occurrence from —CH₃ and —CD₃.

For example, disclosed herein are compounds selected from the group consisting of:

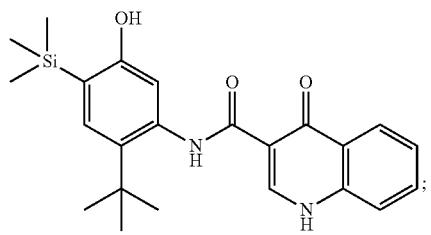

-continued

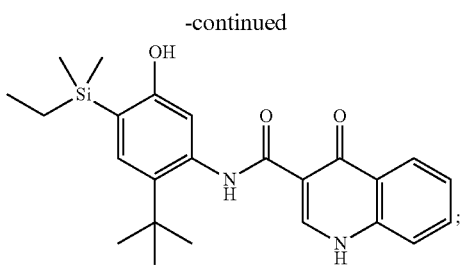

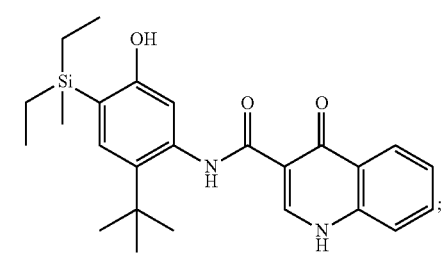

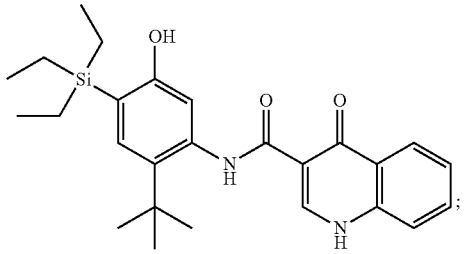

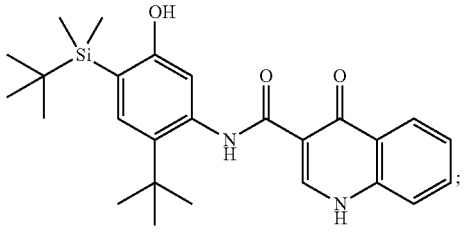

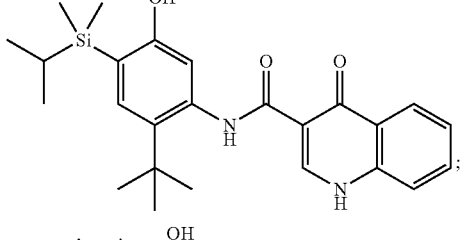

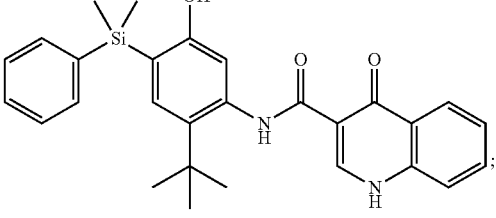

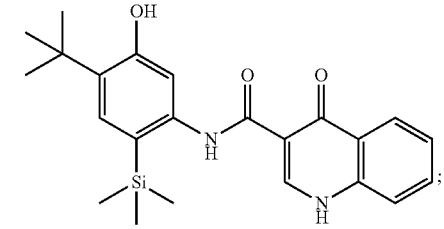

-continued
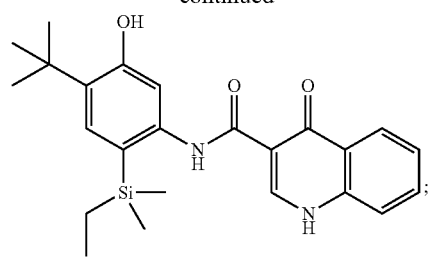
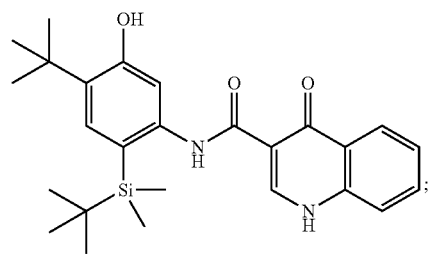
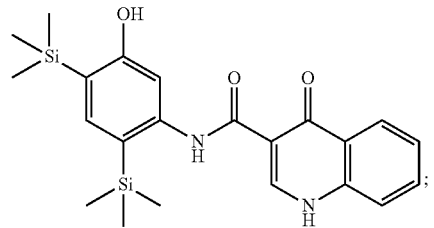
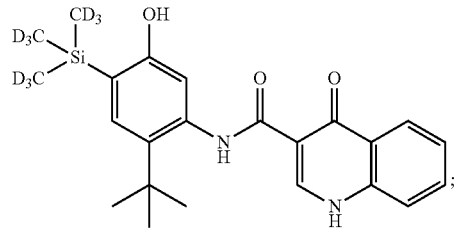
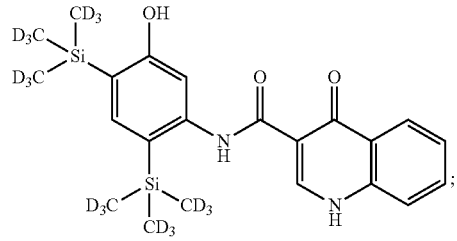
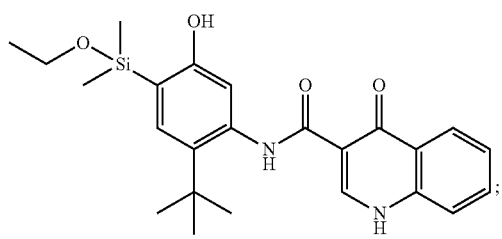
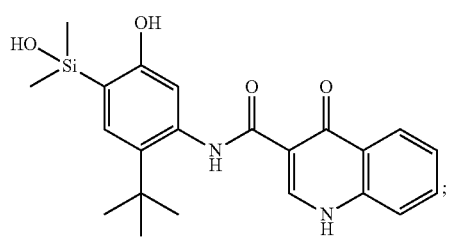
-continued
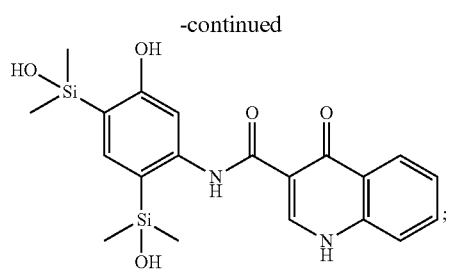
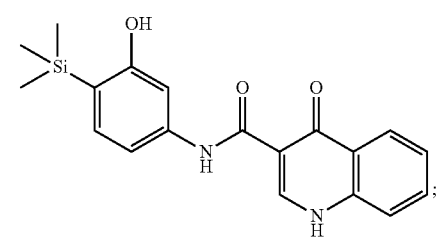
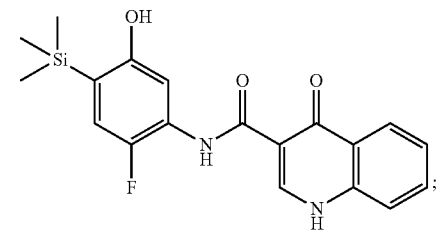
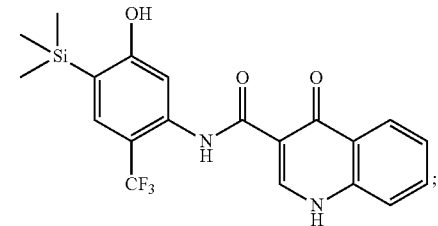
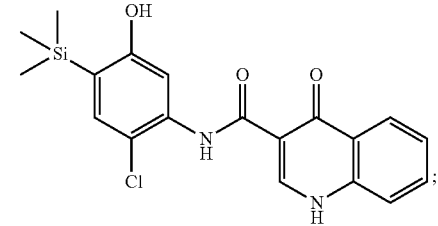
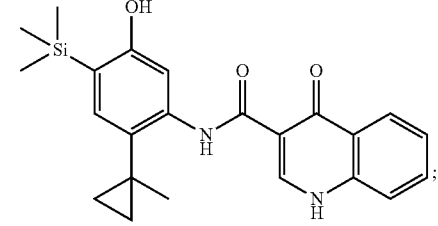
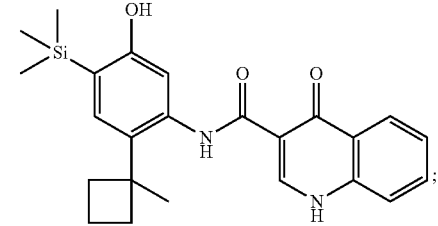

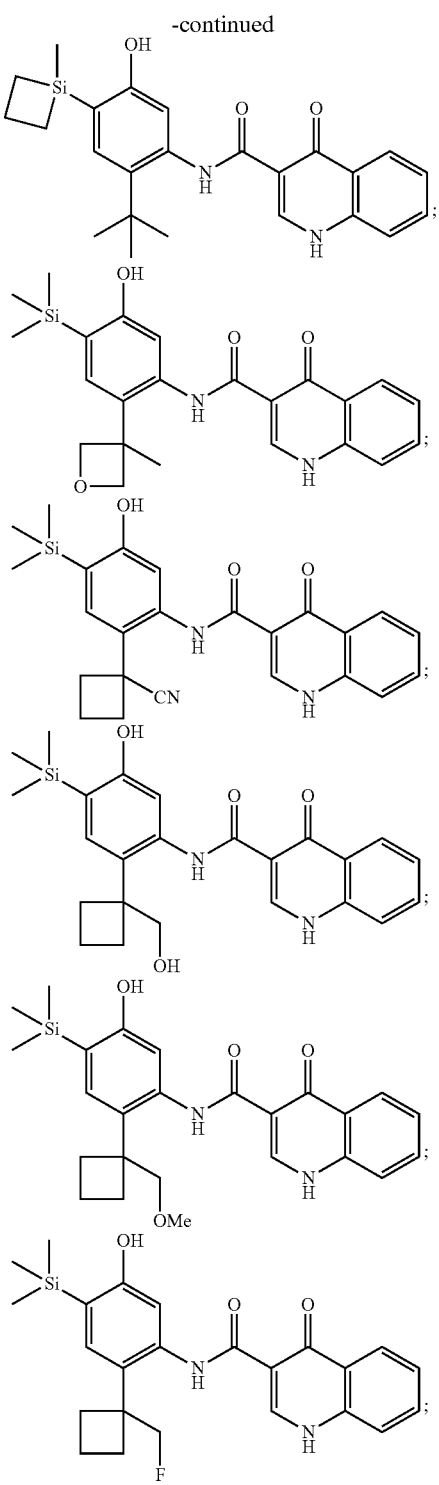

and a pharmaceutically acceptable salt thereof; wherein any atom not designated as deuterium is present at its natural isotopic abundance.

Also contemplated herein are pharmaceutical compositions that include a disclosed compound, e.g., N-(2,4-di-tert-butyl-5-hydroxyphenyl)-4-oxo-1,4-dihydroquinoline-3-carboxamide wherein at least one carbon atom is replaced by silicon, and a pharmaceutically acceptable carrier or excipient. Further contemplated herein are pharmaceutical compositions that include a disclosed compound such as those compounds having Formula I and a pharmaceutically acceptable carrier or excipient. In certain embodiments, the compositions can include at least one additional CFTR modulator as described anywhere herein or at least two additional CFTR modulators, each independently as described anywhere herein.

The features and other details of the disclosure will now be more particularly described. Before further description of the disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

It will be appreciated that the description of the disclosure herein should be construed in congruity with the laws and principals of chemical bonding.

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms, and straight or branched hydrocarbons of 1-6, 1-4, or 1-3 carbon atoms, referred to herein as $C_{1-6}$ alkyl, $C_{1-4}$ alkyl, and $C_{1-3}$ alkyl, respectively. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond. Exemplary alkenyl groups include, but are not limited to, a straight or branched group of 2-6 or 3-4 carbon atoms, referred to herein as $C_{2-6}$ alkenyl, and $C_{3-4}$ alkenyl, respectively. Exemplary alkenyl groups include, but are not limited to, vinyl, allyl, butenyl, pentenyl, etc.

The term, "alkynyl", as used herein, refers to both straight and branched-chain moieties having the specified number or carbon atoms and having at least one carbon-carbon triple bond.

The term "cycloalkyl," as used herein, refers to saturated cyclic alkyl moieties having 3 or more carbon atoms, for example, 3-10, 3-6, or 4-6 carbons, referred to herein as $C_{3-10}$ cycloalkyl, $C_{3-6}$ cycloalkyl or $C_{4-6}$ cycloalkyl, respectively. Examples of cycloalkyl include, but are not limited to, cyclopropyl, cyclobutyl, cyclopentyl, cyclohexyl, cycloheptyl and adamantyl.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

"Alkylene" means a straight or branched, saturated aliphatic divalent radical having the number of carbons indicated. "Cycloalkylene" refers to a divalent radical of carbocyclic saturated hydrocarbon group having the number of carbons indicated.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$ alkoxy, and $C_{2-6}$ alkoxy, respectively. Exemplary alkoxy groups include, but are not limited to methoxy, ethoxy, isopropoxy, etc.

The term "heterocyclic" or "heterocycle" or "heterocyclyl" encompasses heterocycloalkyl, heterocycloalkenyl, heterobicycloalkyl, heterobicycloalkenyl, heteropolycycloalkyl, heteropolycycloalkenyl, and the like unless indicated otherwise. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkenyl groups containing one or more heteroatoms (O, S or N) within a ring, a heterocycle can refer to, for example, a saturated or partially unsaturated 4- to 12 or 4-10-membered ring structure, including bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran, etc.

Cycloalkyl, cycloalkenyl, and heterocyclic groups also include groups similar to those described above for each of these respective categories, but which are substituted with one or more oxo moieties.

The term "heteroaryl", as used herein, refers to aromatic carbocyclic groups containing one or more heteroatoms (O, S, or N) within a ring. A heteroaryl group, unless indicated otherwise, can be monocyclic or polycyclic. A heteroaryl group may additionally be substituted or unsubstituted. Contemplated heteroaryl groups include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is 4- to 12-membered heteroaryl. In yet other embodiments, the heteroaryl is a mono or bicyclic 4- to 10-membered heteroaryl.

The terms "halo" or "halogen" as used herein refer to F, Cl, Br, or I.

The term "haloalkyl" as used herein refers to an alkyl group having 1 to (2n+1) substituent(s) independently selected from F, Cl, Br or I, where n is the maximum number of carbon atoms in the alkyl group. It will be understood that haloalkyl is a specific example of an optionally substituted alkyl.

The terms "hydroxy" and "hydroxyl" as used herein refers to the radical —OH.

As will be understood by the skilled artisan, "H" is the symbol for hydrogen, "D" is the symbol for deuterium, "N" is the symbol for nitrogen, "S" is the symbol for sulfur, "O" is the symbol for oxygen. "Me" is an abbreviation for methyl.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of disclosed compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasterisomers of disclosed compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009. Where a particular compound is described or depicted, it is intended to encompass that chemical structure as well as tautomers of that structure.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

The compounds disclosed herein can exist in solvated as well as unsolvated forms with pharmaceutically acceptable solvents such as water, ethanol, and the like, and it is intended that disclosed compounds include both solvated and unsolvated forms. In one embodiment, a disclosed compound is amorphous or, in another embodiment, a single polymorph. In another embodiment, a disclosed compound is a mixture of polymorphs. In another embodiment, a disclosed compound is in a crystalline form.

Isotopically labeled compounds are also contemplated herein, which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

For example, a disclosed compound may have one or more H atoms replaced with deuterium. It will be recognized that some variation of natural isotopic abundance occurs in a synthesized compound depending upon the origin of chemical materials used in the synthesis. Thus, a preparation of N-(2,4-di-tert-butyl-5-hydroxyphenyl)-4-oxo-1,4-dihydroquinoline-3-carboxamide wherein at least one carbon atom is replaced by silicon, or a preparation of a disclosed compound having Formula I will inherently contain small amounts of deuterated isotopologues. The concentration of naturally abundant stable hydrogen and carbon isotopes, notwithstanding this variation, is small and immaterial as compared to the degree of stable isotopic substitution of compounds of this disclosure.

In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a disclosed compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this disclosure only in the isotopic composition thereof.

The term "compound," when referring to a compound of this disclosure, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of deuterated reagents used to make the compound and the efficiency of incorporation of deuterium in the various synthesis steps used to prepare the compound. However, as set forth above the relative amount of such isotopologues in total will be less than 49.9% of the compound. In other embodiments, the relative amount of such isotopologues in total will be less than 47.5%, less than 40%, less than 32.5%, less than 25%, less than 17.5%, less than 10%, less than 5%, less than 3%, less than 1%, or less than 0.5% of the compound.

Certain isotopically labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are suitable for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be suitable in some circumstances. Isotopically labeled compounds can generally be prepared by following procedures analogous to those disclosed in the examples herein by substituting an isotopically labeled reagent for a non-isotopically labeled reagent.

In some embodiments one or more of the nitrogen atoms of a disclosed compound if present are oxidized to N-oxide.

Representative synthetic routes for the preparation of the compounds disclosed herein are provided throughout the Examples section. As will be understood by the skilled artisan, diastereomers can be separated from the reaction mixture using column chromatography.

As discussed above, contemplated herein in an embodiment is a method of increasing CFTR activity in a subject comprising administering an effective amount of a disclosed compound. Also contemplated herein is a method of treating a patient suffering from a condition associated with CFTR activity comprising administering to said patient an effective amount of a compound described herein.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a method of treatment, an "effective amount" of the therapeutic agent that is sufficient to ameliorate of one or more symptoms of a disorder and/or prevent advancement of a disorder, cause regression of the disorder and/or to achieve a desired effect.

The term "modulating" encompasses increasing, enhancing, inhibiting, decreasing, suppressing, and the like. The terms "increasing" and "enhancing" mean to cause a net gain by either direct or indirect means. As used herein, the terms "inhibiting" and "decreasing" encompass causing a net decrease by either direct or indirect means.

In some examples, CFTR activity is enhanced after administration of a compound described herein when there is an increase in the CFTR activity as compared to that in the absence of the administration of the compound. CFTR activity encompasses, for example, chloride channel activity of the CFTR, and/or other ion transport activity (for example, $HCO_3^-$ transport). In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10 kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). Contemplated patients may have a CFTR mutation(s) from one or more classes, such as without limitation, Class I CFTR mutations, Class II CFTR mutations, Class III CFTR mutations, Class IV CFTR mutations, Class V CFTR mutations, and Class VI mutations. Contemplated subject (e.g., human subject) CFTR genotypes include, without limitation, homozygote mutations (e.g., ΔF508/ΔF508 and R117H/R117H) and compound heterozygote mutations (e.g., ΔF508/G551D; ΔF508/A455E; ΔF508/G542X; Δ508F/W1204X; R553X/W1316X; W1282X/N1303K, 591Δ18/E831X, F508del/R117H/N1303K/3849+10 kbC>T; Δ303K/384; and DF508/G178R).

In certain embodiments, the mutation is a Class I mutation, e.g., a G542X; a Class II/I mutation, e.g., a ΔF508/G542X compound heterozygous mutation. In other embodiments, the mutation is a Class III mutation, e.g., a G551D; a Class II/Class III mutation, e.g., a ΔF508/G551D compound heterozygous mutation. In still other embodiments, the mutation is a Class V mutation, e.g., a A455E; Class II/Class V mutation, e.g., a ΔF508/A455E compound heterozygous mutation. Of the more than 1000 known mutations of the CFTR gene, ΔF508 is the most prevalent mutation of CFTR which results in misfolding of the protein and impaired trafficking from the endoplasmic reticulum to the apical membrane (Dormer et al. (2001). *J Cell Sci* 114, 4073-4081; http://www.genet.sickkids.on.ca/app). In certain embodiments, ΔF508 CFTR activity is enhanced (e.g., increased). In certain embodiments, ΔF508 CFTR activity and/or G542X CFTR activity and/or G551D CFTR activity and/or A455E CFTR activity is enhanced (e.g., increased). An enhancement of CFTR activity can be measured, for example, using literature described methods, including for example, Ussing chamber assays, patch clamp assays, and hBE Ieq assay (Devor et al. (2000), Am J Physiol Cell Physiol 279(2): C461-79; Dousmanis et al. (2002), J Gen Physiol 119(6): 545-59; Bruscia et al. (2005), PNAS 103(8): 2965-2971).

As discussed above, the disclosure also encompasses a method of treating cystic fibrosis. Methods of treating other conditions associated with CFTR activity, including conditions associated with deficient CFTR activity, comprising administering an effective amount of a disclosed compound, are also provided herein.

For example, provided herein is a method of treating a condition associated with deficient or decreased CFTR activity comprising administering an effective amount of a disclosed compound that enhances CFTR activity. Non-limiting examples of conditions associated with deficient CFTR activity are cystic fibrosis, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), chronic sinusitis, dry eye disease, protein C deficiency, Aβ-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, cholestatic liver disease (e.g. Primary biliary cirrhosis (PBC) and primary sclerosing cholangitis (PSC)), and Sjogren's syndrome.

In some embodiments, disclosed methods of treatment further comprise administering an additional therapeutic agent. For example, in an embodiment, provided herein is a method of administering a disclosed compound and at least one additional therapeutic agent. In certain aspects, a disclosed method of treatment comprises administering a disclosed compound, and at least two additional therapeutic agents. Additional therapeutic agents include, for example, mucolytic agents, bronchodilators, antibiotics, anti-infective agents, anti-inflammatory agents, ion channel modulating agents, therapeutic agents used in gene therapy, CFTR correctors, and CFTR amplifiers, or other agents that modulates CFTR activity. In some embodiments, at least one additional therapeutic agent is selected from the group consisting of a CFTR corrector and a CFTR amplifier. Non-limiting examples of CFTR modulators, correctors and amplifiers include VX-152, VX-440, VX-809 (lumacaftor) (3-(6-(1-(2,2-difluorobenzo[d][1,3]dioxol-5-yl)cyclopropanecarboxamido)-3-methylpyridin-2-yl)benzoic acid, VX-661 (1-(2,2-difluoro-1,3-benzodioxol-5-yl)-N-[1-[(2R)-2,3-dihydroxypropyl]-6-fluoro-2-(2-hydroxy-1,1-dimethyl-ethyl)-1H-indol-5-yl]-cyclopropanecarboxamide), VX-983, Ataluren (PTC124) (3-[5-(2-fluorophenyl)-1,2,4-oxadiazol-3-yl]benzoic acid), FDL169, GLPG2222 (for example, a CFTR corrector), GLPG2851, GLPG2665, GLPG2737; and compounds described in, e.g., WO2014/144860 and 2014/176553, hereby incorporated by reference. Non-limiting examples of modulators include GLPG2451, GLPG1837, GLPG3067, QBW-251, QR-010, NB-124, riociquat, and compounds described in, e.g., WO2014/045283; WO2014/081821, WO2014/081820, WO2014/152213; WO2014/160440, WO2014/160478, US2014027933; WO2014/0228376, WO2013/038390, WO2011/113894, WO2013/038386; and WO2014/180562, of which the disclosed modulators in those publications are contemplated as an additional therapeutic agent and incorporated by reference. Non-limiting examples of anti-inflammatory agents include N6022 (3-(5-(4-(1H-imidazol-1-yl) phenyl)-1-(4-carbamoyl-2-methylphenyl)-$^1$H-pyrrol-2-yl) propanoic acid), CTX-4430, N1861, N1785, and N91115.

In some embodiments, the methods described herein can further include administering an additional therapeutic agent or administering at least two additional CFTR therapeutic agents. These therapeutic agents may be selected from any compound or therapeutic agent known to have or that demonstrates advantageous properties when administered with a compound having the same mechanism of action as N-(2,4-di-tert-butyl-5-hydroxyphenyl)-4-oxo-1,4-dihydroquinoline-3-carboxamide, e.g., any therapeutic agent known to be useful for co-administration with N-(2,4-di-tert-butyl-5-hydroxyphenyl)-4-oxo-1,4-dihydroquinoline-3-carboxamide. In some embodiments, the methods described herein can further include administering an additional CFTR modulator or administering at least two additional CFTR modulators. In certain embodiments, at least one CFTR modulator is a CFTR corrector (e.g., VX-809, VX-152, VX-440, VX-661, VX-445, VX-659, VX-983, FDL169, GLPG2851, GLPG2665, GLPG2737, and GLPG2222) or amplifier. In certain of these embodiments, one of the at least two additional therapeutic agents is a CFTR corrector (e.g., VX-809, VX-661 and VX-983) and the other is a CFTR amplifier. In certain of these embodiments, one of the at least two additional therapeutic agents is a CFTR corrector (e.g., GLPG2222) and the other is a CFTR amplifier. In certain of these embodiments, one of the at least two additional therapeutic agents is a CFTR corrector (e.g., VX-809 or VX-661) and the other is a CFTR amplifier. In certain of these embodiments, at least one CFTR modulator is an agent that enhances read-through of stop codons (e.g., NB124 or ataluren). In other embodiments, the methods described herein can further include administrating an epithelial sodium channel (ENaC) inhibitor (e.g., VX-371). In other embodiments, the methods described herein can further include administering gene or RNA therapies, including SHP-636.

Accordingly, in another aspect, this disclosure provides a method of treating a condition associated with deficient or decreased CFTR activity (e.g., cystic fibrosis), which includes administering to a subject in need thereof (e.g., a human patient in need thereof) an effective amount of a disclosed compound and at least one or two additional CFTR therapeutic agent(s) (e.g., at least one or two additional CFTR therapeutic agents, e.g., in which one of the at least one or two additional therapeutic agents is optionally a CFTR corrector, modulator or amplifier (e.g., VX-809, VX-661, VX-983, VX-445, VX-659, GLPG2222, NB124, ataluren); e.g., one of the at least two additional therapeutic agents is GLPG2222, and the other is GLPG1837 or GLPG3067; or one of the at least two additional therapeutic agents is VX-809 or VX-661. Additional agents, e.g. amplifiers, are disclosed in co-pending applications PCT/US14/044100, PCT/US15/020460, PCT/US15/020499, and PCT/US15/036691, each incorporated by reference. For example, an exemplary amplifier is N-(3-(5-(hydroxymethyl)-1H-1,2,3-triazol-1-yl)propyl)-5-phenylisoxazole-3-carboxamide ("Compound A"). In certain embodiments, the subject's CFTR genotype includes, without limitation, one or more Class I CFTR mutations, one or more Class II CFTR mutations, one or more Class III CFTR mutations, one or more Class IV CFTR mutations, or one or more Class V CFTR mutations, or one or more Class VI CFTR mutations. In certain embodiments, the subject's CFTR genotype includes, without limitation, one or more homozygote mutations (e.g., ΔF508/ΔF508 or R117H/R117H) and/or one or more compound heterozygote mutations (e.g., ΔF508/G551D; ΔF508/A455E; ΔF508/G542X; Δ508F/W1204X; R553X/W1316X; W1282X/N1303K; F508del/R117H; N1303K/3849+10 kbC>T; ΔF508/R334W; DF508/G178R, and 591Δ18/E831X). In certain embodiments, the subject's CFTR genotype includes a Class I mutation, e.g., a G542X Class I mutation, e.g., a ΔF508/G542X compound heterozygous mutation. In other embodiments, the subject's CFTR genotype includes a Class III mutation, e.g., a G551D Class III mutation, e.g., a ΔF508/G551D compound heterozygous mutation. In still other embodiments, the subject's CFTR genotype includes a Class V mutation, e.g., a A455E Class V mutation, e.g., a ΔF508/A455E compound heterozygous mutation. In certain embodiments, ΔF508 CFTR activity and/or G542X CFTR activity and/or G551D CFTR activity and/or A455E activity is enhanced (e.g., increased). In certain embodiments, the enhancement in activity (e.g., increase in activity) provided by the combination of the disclosed compound and one or two additional therapeutic agents is greater than additive when compared to the enhancement in activity provided by each therapeutic component individually.

| Class | Effect on CFTR protein | Example of mutation |
|---|---|---|
| I | Shortened protein | W1282X Instead of inserting the amino acid tryptophan (W), the protein sequence is prematurely stopped (indicated by an X). |
| II | Protein fails to reach cell membrane | ΔF508 A phenylalanine amino acid (F) is deleted |
| III | Channel cannot be regulated properly | G551D A "missense" mutation: instead of a glycine amino acid (G), aspartate (D) is added |
| IV | Reduced chloride conductance | R117H Missense |
| V | Reduced due to incorrect splicing of gene | 3120 + 1G > A Splice-site mutation in gene intron 16 |
| VI | Reduced due to protein instability | N287Y a A -> T at 991 |

| Genotype | Description | Possible Symptoms |
|---|---|---|
| Δ508F/Δ508F | homozygote | Severe lung disease, pancreatic insufficient |
| R117H/R117H | homozygote | Congenital bilateral absence of the vas deferens, No lung or pancreas disease, |
| WT/Δ508F | heterozygote | Unaffected |
| WT/3120 + 1 G > A | heterozygote | Unaffected |
| Δ508F/W1204X | compound heterozygote | No lung disease, pancreatic insufficient |
| R553X and W1316X | compound heterozygote | Mild lung disease, pancreatic insufficient |
| 591Δ18/E831X | compound heterozygote | No lung or pancreas disease, nasal polyps |

For example, provided herein is a method of treating a patient having one or more of the following mutations in the CFTR gene: G1244E, G1349D, G178R, G551S, S1251N, S1255P, S549N, S549R, G970R, or R117H, G551D, and/or G167R, and/or e.g., a patient with one or two copies of the F508del mutation, or one copy of the ΔF508 mutation and a second mutation that results in a gating effect in the CFTR protein (e.g., a patient that is heterozygous for ΔF508 and G551D mutation), a patient with one copy of the ΔF508 mutation and a second mutation that results in residual CFTR activity, or a patient with one copy of the ΔF508 mutation and a second mutation that results in residual CFTR activity, comprising administering an effective amount of a disclosed compound. As described herein, such exemplary methods (e.g., of a patient having one or mutations such as those described above) may include, for example, administering to such patient a combination therapy, e.g., administering (simultaneously or sequentially) an effective amount of VX-661 or lumacaftor to said patient and an effective amount of a disclosed compound that may act as a potentiator or a disclosed compound that may act as an amplifier. Such administration may result, for example, in increased chloride transport in human bronchial epithelial cells with e.g., one or two copies of mutations, e.g, ΔF508 mutation, as compared to administration of lumacaftor or ivacaftor alone. Another combination therapy that includes a disclosed compound may also include an effective amount of a readthrough agent (e.g., ataluren, NB124) and an effect amount of disclosed compound that may act as an amplifier or as a corrector.

The phrase "combination therapy," as used herein, refers to an embodiment where a patient is co-administered a disclosed compound, a CFTR amplifier, and optionally, one or more CFTR corrector agent(s) (e.g, VX-661 and/or lumacaftor) as part of a specific treatment regimen intended to provide the beneficial effect from the co-action of these therapeutic agents. For example, a beneficial effect of a combination may include, but is not limited to, pharmacokinetic or pharmacodynamic co-action resulting from the combination of therapeutic agents. For example, administration of a disclosed compound with an amplifier alone or with a CFTR corrector agent (e.g., lumacaftor or VX-661) may result in a level of function (e.g., as measured by chloride activity in HBE cells or patients that have a ΔF508 mutation, that achieves clinical improvement (or better) as compared to the chloride activity level in cells or patients with a G551D mutation receiving a corrector agent alone (e.g., lumacaftor or VX-661). Administration of disclosed therapeutic agents in combination typically is carried out over a defined time period (usually a day, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, inhalational routes, intravenous routes, intramuscular routes, and direct absorption through mucous membrane tissues. The therapeutic agents can be administered by the same route or by different routes. For example, a first therapeutic agent of the combination selected may be administered by intravenous injection or inhalation or nebulizer while the other therapeutic agents of the combination may be administered orally. Alternatively, for example, all therapeutic agents may be administered orally or all therapeutic agents may be administered by intravenous injection, inhalation or nebulization.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by a day, days or even weeks.

The components of a disclosed combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

The term "pharmaceutically acceptable salt(s)" as used herein refers to salts of acidic or basic groups that may be present in a disclosed compounds used in disclosed compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

In an embodiment, contemplated methods may include for example, administering prodrugs of the compounds described herein, for example, prodrugs of a compound of Formula I, or a pharmaceutical composition thereof.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., *Nature Reviews Drug Discovery* 2008, 7, 255). For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino-$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-(($C_{1-6}$)alkylcarbonyloxy)ethyl, 1-methyl-1-(($C_{1-6}$)alkylcarbonyloxy)ethyl $(C_{1-6})$alkoxycarbonyloxy)methyl, N—$(C_{1-6})$alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-amino-alkylcarbonyl-α-aminoalkylcarbonyl, where each α-aminoalkylcarbonyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplício, et al., *Molecules* 2008, 13, 519 and references therein.

Also contemplated in certain embodiments is the use of clathrates of the compounds described herein, pharmaceutical compositions comprising the clathrates, and methods of use of the clathrates. Clathrates of a disclosed compound or a pharmaceutical composition thereof are also contemplated herein.

As discussed above, the disclosure also contemplates administration of pharmaceutical compositions comprising a pharmaceutically acceptable carrier or excipient and a compound described herein. A disclosed compound, or a pharmaceutically acceptable salt, solvate, clathrate or prodrug thereof, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be suitable for treatment of a systemic disorder and oral administration may be suitable to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. A pharmaceutical composition comprising a disclosed compound or a pharmaceutically acceptable salt, solvate, clathrate or prodrug, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

Disclosed compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfate and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are suitable liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, or about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present disclosure, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The disclosure also encompasses the treatment of a condition associated with a dysfunction in proteostasis in a subject comprising administering to said subject an effective amount of a disclosed compound that enhances, improves or restores proteostasis of a protein. Proteostasis refers to protein homeostasis. Dysfunction in protein homeostasis is a result of protein misfolding, protein aggregation, defective protein trafficking or protein degradation. For example, the disclosure contemplates s administering a disclosed compound e.g., Formula I that corrects protein misfolding, reduces protein aggregation, corrects or restores protein trafficking and/or affects protein degradation for the treatment of a condition associated with a dysfunction in proteostasis. In some aspects, a disclosed compound e.g., Formula I that corrects protein misfolding and/or corrects or restores protein trafficking is administered. In cystic fibrosis, the mutated or defective enzyme is the cystic fibrosis transmembrane conductance regulator (CFTR). One of the most common mutations of this protein is $\Delta$F508 which is a deletion ($\Delta$) of three nucleotides resulting in a loss of the amino acid phenylalanine (F) at the 508th (508) position on the protein. As described above, mutated cystic fibrosis transmembrane conductance regulator exists in a misfolded state and is characterized by altered trafficking as compared to the wild type CFTR. Additional exemplary proteins of which there can be a dysfunction in proteostasis, for example that can exist in a misfolded state, include, but are not limited to, glucocerebrosidase, hexosamine A, aspartylglucosaminidase, $\alpha$-galactosidase A, cysteine transporter, acid ceremidase, acid $\alpha$-L-fucosidase, protective protein, cathepsin A, acid $\beta$-glucosidase, acid $\beta$-galactosidase, iduronate 2-sulfatase, $\alpha$-L-iduronidase, galactocerebrosidase, acid $\alpha$-mannosidase, acid $\beta$-mannosidase, arylsulfatase B, arylsulfatase A, N-acetylgalactosamine-6-sulfate sulfatase, acid $\beta$-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, TDP-43, superoxide dismutase (SOD), Aβ peptide, tau protein, transthyretin and insulin. The compounds of Formula I can be used to restore proteostasis (e.g., correct folding and/or alter trafficking) of the proteins described above.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to, neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tauopathies (progressive supranuclear palsy, corticobasal degeneration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy. Alzheimer's disease is characterized by the formation of two types of aggregates: extracellular aggregates of Aβ peptide and intracellular aggregates of the microtubule associated protein tau. Transtyretin-associated aggregation diseases include, for example, senile systemic amyloidoses and familial amyloidotic neuropathy. Lewy body diseases are characterized by an aggregation of α-synuclein protein and include, for example, Parkinson's disease, lewy body dementia (LBD) and multiple system atrophy (SMA). Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. In another embodiment, the misfolded protein is alpha-1 anti-trypsin.

In a further embodiment, the protein conformation disease is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In another embodiment, a disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, a treatment of a disease associated with a dysfunction in proteostasis is diabetes and/or complications of diabetes, including, but not limited to, diabetic retinopathy, cardiomyopathy, neuropathy, nephropathy, and impaired wound healing is contemplated.

In a further embodiment, a treatment of a disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration is contemplated.

In yet additional embodiments, a disclosed method is directed to treating a disease associated with a dysfunction in proteostasis, wherein the disease affects the respiratory system or the pancreas. In certain additional embodiments, a contemplated method encompass treating a condition selected from the group consisting of polyendocrinopathy/hyperinsulinemia, diabetes mellitus, Charcot-Marie Tooth syndrome, Pelizaeus-Merzbacher disease, and Gorham's Syndrome.

Additional conditions associated with a dysfunction of proteostasis include hemoglobinopathies, inflammatory diseases, intermediate filament diseases, drug-induced lung damage and hearing loss. For example, provided herein are methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage). In another embodiment, methods for treating hearing loss, such as noise-induced hearing loss, aminoglycoside-induced hearing loss, and cisplatin-induced hearing loss comprising administering a disclosed compound are provided.

Additional conditions include those associated with a defect in protein trafficking and that can be treated according to a disclosed methods include: PGP mutations, hERG trafficking mutations, nephrongenic diabetes insipidus mutations in the arginine-vasopressin receptor 2, persistent hyperinsulinemic hypoglycemia of infancy (PHH1) mutations in the sulfonylurea receptor 1, and α1AT.

The disclosure is illustrated by the following examples which are not meant to be limiting in any way.

EXEMPLIFICATION

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as "intermediates" herein are contemplated as compounds of the disclosure.

General Procedures:

General procedures for the preparation of compounds of the invention are outlined in Schemes I-IV. The disclosed compounds may be prepared, for example, through transition metal-catalyzed coupling of a suitably substituted silyl reagent with a suitably functionalized phenol derivative followed by nitro reduction and amide coupling (Scheme I), or through transition metal-catalyzed coupling of a suitably substituted silyl reagent with a suitably functionalized quinolone carboxamide (Schemes II-IV).

Scheme I:

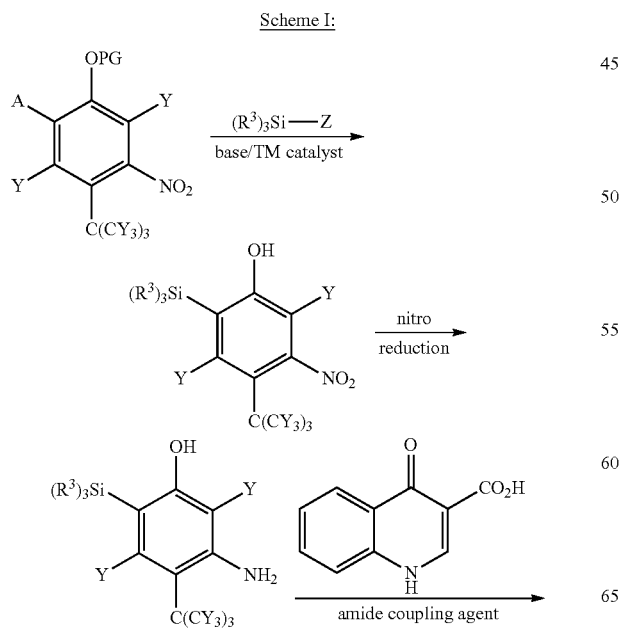

-continued

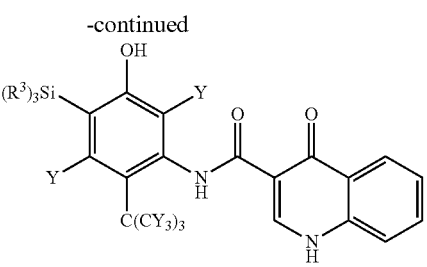

Scheme II:

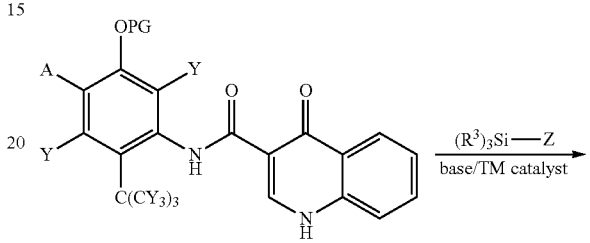

Scheme III:

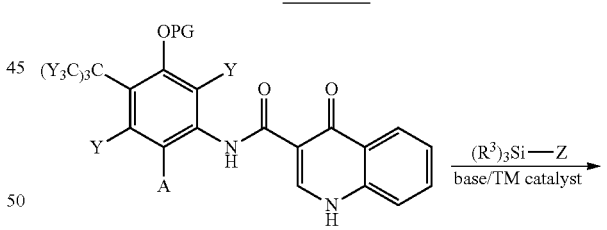

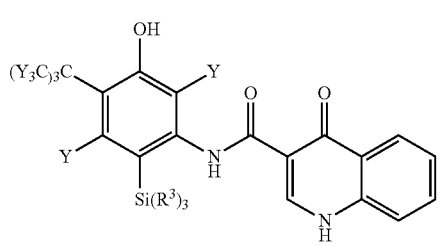

Scheme IV:

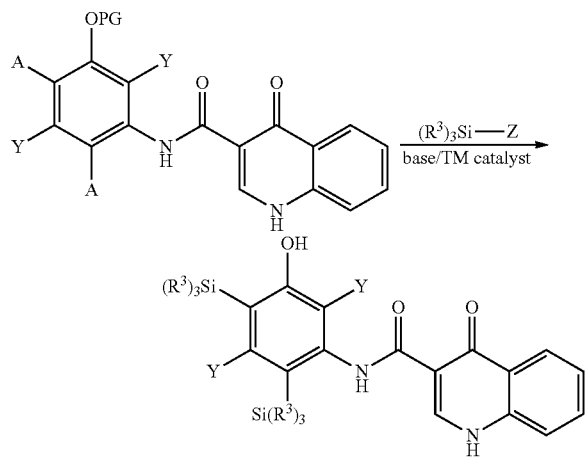

List of Abbreviations

| Abbreviation | Name |
| --- | --- |
| rt | room temperature |
| THF | tetrahydrofuran |
| MeCN | acetonitrile |
| DMPU | 1,3-dimethyl-3,4,5,6-tetrahydro-2(1H)-pyrimidinone |
| DCM | dichloromethane |
| MeOH | methanol |
| EtOAc | ethyl acetate |
| DMF | N,N-dimethylformamide |
| DMAP | 4-(dimethylamino)pyridine |
| AcOH | acetic acid |
| NaOAc | sodium acetate |
| HATU | 1-[Bis(dimethylamino)methylene]-1H-1,2,3-triazolo[4,5-b]pyridinium-3-oxide hexafluorophosphate |
| DIEA | N,N-diisopropylethylamine |
| TEA | triethylamine |
| dba | dibenzylideneacetone |
| cod | cis,cis-1,5-cyclooctadiene |
| JohnPhos | (2-biphenyl)di-tert-butylphosphine |
| Ni(OAc)$_2$ | nickel(II) acetate |
| NIS | N-iodosuccinimide |
| atm | atmosphere |
| NaBH(OAc)$_3$ | sodium triacetoxyborohydride |
| conc | concentrated |
| ESI | Electrospray Ionization |
| pos | positive |
| neg | negative |
| Calcd. | Calculated |

Example 1: Preparation of N-[2-tert-Butyl-5-hydroxy-4-(trimethylsilyl)phenyl]-4-oxo-1,4-dihydroquinoline-3-carboxamide (Compound 1)

A. 2-Bromo-4-tert-butylphenyl methyl carbonate. To a 500-mL round-bottom flask was placed a solution of 2-bromo-4-tert-butylphenol (60 g, 263.1 mmol), TEA (53.145 g, 525 mmol), and DMAP (321 mg, 26.31 mmol) in DCM (900 mL) then the solution was cooled to 0° C. and methyl chloroformate (29.7 g, 315 mmol) was added dropwise with stirring. The reaction was stirred for 5 h at 0° C., quenched by the addition of 500 mL of water/ice, and extracted with DCM (3×500 mL). The organic extracts were combined, dried over anhydrous Na$_2$SO$_4$, and concentrated under reduced pressure. The residue was purified by column chromatography eluting with EtOAc/petroleum ether (1:100-2:100) affording 60.6 g of the title compound as a light yellow oil.

B. 2-Bromo-4-tert-butyl-5-nitrophenyl methyl carbonate. To concentrated sulfuric acid (500 mL) cooled to 0° C. was added 2-bromo-4-tert-butylphenyl methyl carbonate (20 g, 69.9 mmol, as prepared in the previous step), in small portions. After completion of addition, KNO$_3$ (8.474 g, 83.9 mmol) was added in small portions at a rate that maintained the temperature below 0° C. The reaction was stirred for 2 h at rt then poured into 100 mL of water/ice and extracted with DCM (3×100 mL). The organic extracts were combined, dried over anhydrous Na$_2$SO$_4$, and concentrated under reduced pressure. The residue was purified by column chromatography eluting with EtOAc/petroleum ether (1:9) affording 20 g of the title compound as a light yellow oil. $^1$H NMR (400 MHz, CDCl$_3$): δ 7.80 (s, 1H), 7.31 (s, 1H), 5.32 (s, 1H), 4.00 (s, 3H), 1.48 (s, 9H).

C. 4-tert-Butyl-5-nitro-2-(trimethylsilyl)phenol. To a 40-mL vial purged and maintained with an inert atmosphere of nitrogen, was placed a solution of 2-bromo-4-tert-butyl-5-nitrophenyl methyl carbonate (1 g, 3.01 mmol, as prepared in the previous step), hexamethyldisilane (8.8 g, 60 mmol), Pd$_2$(dba)$_3$.CHCl$_3$ (155 mg, 0.15 mmol), JohnPhos (134 mg, 0.45 mmol), and KF/Al$_2$O$_3$ (50%, 1.205 g) in DMPU (10 mL). The reaction was stirred for 6 h at 110° C. then cooled to rt and filtered. The filtrate was diluted with 100 mL of water and extracted with EtOAc (3×50 mL). The organic extracts were combined, dried over anhydrous Na$_2$SO$_4$, and concentrated under reduced pressure. This reaction was repeated an additional 49 times then the combined crude product was purified by column chromatography eluting with EtOAc/petroleum ether (1:20) affording 30 g of 4-tert-butyl-5-nitro-2-(trimethylsilyl)phenol as a yellow solid. Mass Spectrum (LCMS, ESI pos): Calcd. for C$_{13}$H$_{22}$NO$_3$Si$^+$: 268.1 (M+H); Found: 268.1.

D. 5-Amino-4-tert-butyl-2-(trimethylsilyl)phenol. To a 500-mL round-bottom flask was placed a solution of 4-tert-butyl-5-nitro-2-(trimethylsilyl)phenol (10 g, 37.5 mmol, as prepared in the previous step) and Ni(OAc)$_2$ (10 g, 56.8 mmol) in MeOH/THF (80/80 mL) then the solution was cooled to 0° C. and NaBH$_4$ (5 g, 132 mmol) was added in portions. The reaction was stirred for 30 min at rt then the solids were removed by filtration. The filtrate was with 300 mL of saturated aqueous NH$_4$Cl solution and extracted with EtOAc (3×300 mL). The organic extracts were combined, dried over anhydrous Na$_2$SO$_4$, and then diluted with 150 mL of DMF. The resulting solution was concentrated under reduced pressure to remove the low boiling solvents affording a DMF solution of the title compound, which was used directly in the next step. This reaction was repeated an additional 2 times and the 3 batches were combined. Mass Spectrum (LCMS, ESI pos): Calcd. for C$_{13}$H$_{24}$NOSi$^+$: 238.2 (M+H); Found: 238.2.

E. N-[2-tert-Butyl-5-hydroxy-4-(trimethylsilyl)phenyl]-4-oxo-1,4-dihydroquinoline-3-carboxamide. To a 1-L round-bottom flask, was placed a solution of 5-amino-4-tert-butyl-2-(trimethylsilyl)phenol in DMF (450 mL, as prepared in the previous step), then 4-oxo-1,4-dihydroquinoline-3-carboxylic acid (21 g, 0.11 mol), HATU (50 g, 0.13 mol), and TEA (33 g, 0.33 mol) were added. The reaction was stirred for 48 h at rt then diluted with 300 mL of water and extracted with EtOAc (3×300 mL). The organic extracts were combined, dried over anhydrous Na$_2$SO$_4$, and concentrated under reduced pressure. The crude product was purified by Prep-HPLC (HPLC-10: Column, X Bridge C18 OBD Prep Column, 19 mm×250 mm; mobile phase, Water (10 mmol/L NH$_4$HCO$_3$) and MeCN (70% MeCN up to 90% in 6 min); Detector, UV 254/220 nm) affording 5.13 g of the title compound as a white solid. Mass Spectrum (LCMS, ESI pos): Calcd. for C$_{23}$H$_{29}$N$_2$O$_3$Si$^+$: 409.2 (M+H); Found: 409.1. $^1$H NMR (300 MHz, DMSO-d$_6$): δ 12.90 (s, 1H), 11.91 (s, 1H), 9.28 (s, 1H), 8.88 (s, 1H), 8.35-8.32 (m, 1H), 7.82-7.74 (m, 2H), 7.55-7.49 (m, 1H), 7.26 (s, 1H), 7.16 (s, 1H), 1.39 (s, 9H), 0.25 (s, 9H). HPLC purity (254 nm): 96.2%.

Example 2: Preparation of N-[2-tert-Butyl-4-(ethyldimethylsilyl)-5-hydroxyphenyl]-4-oxo-1,4-dihydroquinoline-3-carboxamide (Compound 2)

A. 4-Oxo-1,4-dihydroquinoline-3-carbonyl chloride. To a 500-mL round-bottom flask was placed a solution of 4-oxo-1,4-dihydroquinoline-3-carboxylic acid (6 g, 31.72 mmol) in DCM (250 mL), TEA (6.4 g, 63.25 mmol) then the solution was cooled to 0° C. and thionyl chloride (7.49 g) was added dropwise with stirring. The reaction was stirred for 2 h at 50° C. then concentrated under reduced pressure affording 5.5 g of the title compound as a white solid.

B. 3-Amino-4-tert-butylphenyl methyl carbonate. To a 500-mL round-bottom flask was placed a solution of 2-bromo-4-tert-butyl-5-nitrophenyl methyl carbonate (10 g, 30.11 mmol, as prepared in Example 1, Step B) in MeOH (300 mL) then Pd on carbon (1 g) was added. The resulting solution was degassed and back-filled with H$_2$ (5 atm) and stirred for 16 h at rt. The H$_2$ was purged then the solids were removed by filtration. The filtrate was concentrated under reduced pressure affording 6.3 g of the title compound as a brown solid. Mass Spectrum (LCMS, ESI pos): Calcd. for C$_{12}$H$_{18}$NO$_3$$^+$: 224.1 (M+H); Found: 224.1.

C. 5-Amino-4-tert-butyl-2-iodophenyl methyl carbonate. To a 100-mL round-bottom flask was placed a solution of 3-amino-4-tert-butylphenyl methyl carbonate (6.3 g, 28.22 mmol, as prepared in the previous step) and NIS (4.5 g, 20.00 mmol) in DMF (40 mL). The reaction was stirred for 1.5 h at rt, quenched by the addition of 50 mL of water, and extracted with EtOAc (3×50 mL). The organic extracts were combined and concentrated under reduced pressure. The residue was purified by column chromatography eluting with EtOAc/petroleum ether (1:2) affording 9.1 g of the title compound as a brown oil. Mass Spectrum (LCMS, ESI pos): Calcd. for C$_{12}$H$_{17}$INO$_3$$^+$: 350.0 (M+H); 350.0.

D. 4-tert-Butyl-2-iodo-5-(4-oxo-1,4-dihydroquinoline-3-amido)phenyl methyl carbonate. To a 250-mL round-bottom flask was placed a solution of 5-amino-4-tert-butyl-2-iodophenyl methyl carbonate (3.49 g, 10.00 mmol, as prepared in the previous step) and DIEA (3.225 g, 24.95 mmol) in DCM (100 mL) then 4-oxo-1,4-dihydroquinoline-3-carbonyl chloride (4.14 g, 19.94 mmol, as prepared in Step A) was added. The reaction was stirred for 2 days at rt, then washed with water (3×50 mL), dried over Na$_2$SO$_4$, and concentrated under reduced pressure. The residue was purified by column chromatography eluting with DCM/MeOH (20:1) affording 1.2 g of the title compound as a brown solid. Mass Spectrum (LCMS, ESI pos): Calcd. for C$_{22}$H$_{22}$IN$_2$O$_5$$^+$: 521.1 (M+H); Found: 521.0.

E. N-[2-tert-Butyl-4-(ethyldimethylsilyl)-5-hydroxyphenyl]-4-oxo-1,4-dihydroquinoline-3-carboxamide. To a 8-mL sealed tube purged and maintained with an inert atmosphere of nitrogen, was placed a solution of 4-tert-butyl-2-iodo-5-(4-oxo-1,4-dihydroquinoline-3-amido)phenyl methyl carbonate (200 mg, 0.38 mmol, as prepared in the previous step) in DMPU (2.5 mL) then ethyldimethylsilane (136 mg, 1.54 mmol), [Rh(cod)$_2$]BF$_4$ (8 mg, 0.02 mmol), and K$_3$PO$_4$ (123 mg, 0.58 mmol) were added. The reaction was stirred for 16 h at 60° C. then cooled to rt and filtered. The filtrate was diluted with 50 mL of water then extracted with EtOAc (3×50 mL). The organic extracts were combined, dried over anhydrous Na$_2$SO$_4$, and concentrated under reduced pressure. The crude product was purified by Prep-HPLC (HPLC-10: Column, X Bridge C18 OBD Prep Column, 10 um, 19 mm×250 mm; mobile phase, Water (10 mmol/L NH$_4$HCO$_3$) and MeCN (60.0% MeCN up to 81.0% in 10 min); Detector, UV 254/220 nm) affording 12.7 mg of the title compound as a gray solid. Mass Spectrum (LCMS, ESI pos): Calcd. for C$_{24}$H$_{31}$N$_2$O$_3$Si$^+$: 423.2 (M+H); Found: 423.2. $^1$H NMR (400 MHz, DMSO-d$_6$): δ 12.90 (d, J=6.8 Hz, 1H), 11.90 (s, 1H), 9.25 (s, 1H), 8.70 (d, J=6.4 Hz, 1H), 8.33 (d, J=8.4 Hz, 1H), 7.90-7.70 (m, 2H), 7.52 (t, J=7.6 Hz, 1H), 7.25 (s, 1H), 7.16 (s, 1H), 1.39 (s, 9H), 0.94 (t, J=7.6 Hz, 3H), 0.76 (q, J=7.6 Hz, 2H), 0.22 (s, 6H). HPLC purity (254 nm): 96.9%.

Example 3: Preparation of N-[2-tert-Butyl-4-[diethyl(methyl)silyl]-5-hydroxyphenyl]-4-oxo-1,4-dihydroquinoline-3-carboxamide (Compound 3)

A. N-[2-tert-Butyl-4-[diethyl(methyl)silyl]-5-hydroxyphenyl]-4-oxo-1,4-dihydroquinoline-3-carboxamide. To a 20-mL sealed tube purged and maintained with an inert atmosphere of nitrogen, was placed a solution of 4-tert-butyl-2-iodo-5-(4-oxo-1,4-dihydroquinoline-3-amido)phenyl methyl carbonate (200 mg, 0.38 mmol, as prepared in Example 2, Step D) in DMPU (2.5 mL) then diethyl(methyl)silane (157 mg, 1.54 mmol), [Rh(cod)$_2$]BF$_4$ (7.8 mg, 0.02 mmol) and K$_3$PO$_4$ (123 mg, 0.58 mmol) were added. The reaction was stirred for 16 h at 60° C. then cooled to rt and filtered. The filtrate was diluted with 50 mL of water then extracted with EtOAc (3×50 mL). The organic extracts were combined, dried over anhydrous Na$_2$SO$_4$, and concentrated under reduced pressure. The crude product was purified by Prep-HPLC (HPLC-10: Column, X Bridge C18 OBD Prep Column, 10 μm, 19 mm×250 mm; mobile phase, Water (10 mmol/L NH$_4$HCO$_3$) and MeCN (63.0% MeCN up to 85.0% in 10 min); Detector, UV 254/220 nm) affording 20.2 mg of the title compound as a gray solid. Mass Spectrum (LCMS, ESI pos): Calcd. for C$_{25}$H$_{33}$N$_2$O$_3$Si$^+$: 437.2 (M+H); Found: 437.2. $^1$H NMR (400 MHz, DMSO-d$_6$): δ 12.90 (d, J=6.4 Hz, 1H), 11.90 (s, 1H), 9.23 (s, 1H), 8.87 (d, J=6.8 Hz, 1H), 8.33 (d, J=8.0 Hz, 1H), 7.90-7.70 (m, 2H), 7.52 (t, J=7.6 Hz, 1H), 7.25 (s, 1H), 7.17 (s, 1H), 1.39 (s, 9H), 0.94 (t, J=8.0 Hz, 6H), 0.77 (q, J=7.6 Hz, 4H), 0.20 (s, 3H). HPLC purity (254 nm): 98.7%.

Example 4: Preparation of N-(2-(tert-Butyl)-5-hydroxy-4-(triethylsilyl)phenyl)-4-oxo-1,4-dihydroquinoline-3-carboxamide (Compound 4)

A. 5-Amino-2-bromo-4-tert-butylphenyl methyl carbonate. To a 100-mL round-bottom flask was placed a solution of 2-bromo-4-tert-butyl-5-nitrophenyl methyl carbonate (3.3 g, 10 mmol, as prepared in Example 1, Step B) in THF/AcOH (60/15 mL) then Fe (2.8 g, 50 mmol) was added. The reaction was stirred for 5 h at rt then the solids were removed by filtration. The filtrate was concentrated under reduced pressure. The residue was purified by column chromatography eluting with EtOAc/petroleum ether (1:10) affording 2.6 g of the title compound as a yellow solid. Mass Spectrum (LCMS, ESI pos): Calcd. for C$_{12}$H$_{17}$BrNO$_3$$^+$: 302.0 (M+H); Found: 302.1.

B. 2-Bromo-4-tert-butyl-5-(4-oxo-1,4-dihydroquinoline-3-carboxamido)phenyl methyl carbonate. To a 100-mL round-bottom flask was placed a solution of 5-amino-2-bromo-4-tert-butylphenyl methyl carbonate (1.5 g, 5 mmol, as prepared in the previous step) in DMF (20 mL) then 4-oxo-1,4-dihydroquinoline-3-carboxylic acid (1.5 g, 7.5 mmol), HATU (2.9 g, 7.5 mmol), and DIEA (19 g, 15 mmol) were added. The reaction was stirred for 16 h at rt then diluted with 100 mL of water, and extracted with EtOAc (3×100 mL). The organic extracts were combined, dried over anhydrous $Na_2SO_4$, and concentrated under reduced pressure. The residue was purified by column chromatography eluting with EtOAc/petroleum ether (1:5) affording 1.4 g of the title compound as a grey solid. Mass Spectrum (LCMS, ESI pos): Calcd. for $C_{22}H_{22}BrN_2O_5^+$: 473.1 (M+H); Found: 473.2.

C. N-(2-(tert-Butyl)-5-hydroxy-4-(triethylsilyl)phenyl)-4-oxo-1,4-dihydroquinoline-3-carboxamide. To a 20-mL sealed tube purged and maintained with an inert atmosphere of nitrogen, was placed a solution of 2-bromo-4-tert-butyl-5-(4-oxo-1,4-dihydroquinoline-3-amido)phenyl methyl carbonate (600 mg, 1.27 mmol, as prepared in the previous step) in DMPU (4.5 mL) then $Pd_2(dba)_3 \cdot CHCl_3$ (39 mg, 0.04 mmol), JohnPhos (57 mg, 0.19 mmol), $KF/Al_2O_3$ (50%, 737 mg, 12.71 mmol), and triethylsilane (589 mg, 5.07 mmol) were added. The reaction was stirred for 16 h at 90° C., cooled to rt, and filtered. The filtrate was diluted with 100 mL of water and extracted with EtOAc (3×50 mL). The organic extracts were combined, dried over anhydrous $Na_2SO_4$, and concentrated under reduced pressure. The crude product was purified by Prep-HPLC (HPLC-10: Column, X Select CSH Prep C18 OBD Column, 5 um, 19*150 mm; mobile phase, Water (10 mmol/L $NH_4HCO_3$) and MeCN (50.0% MeCN up to 76.0% in 1 min, up to 95.0% in 7 min); Detector, UV 254/220 nm) affording 8.6 mg of the title compound as a white solid. Mass Spectrum (LCMS, ESI pos): Calcd. for $C_{26}H_{35}N_2O_3Si^+$: 451.2 (M+H); Found: 451.3. $^1$H NMR (400 MHz, DMSO-$d_6$): δ 12.94 (brs, 1H), 12.02 (s, 1H), 8.91 (s, 1H), 8.33 (d, J=7.2 Hz, 1H), 7.85-7.70 (m, 2H), 7.51 (t, J=8.0 Hz, 1H), 7.34 (d, J=2.8 Hz, 1H), 7.25 (d, J=8.8 Hz, 1H), 6.63 (dd, J=2.8, 8.4 Hz, 1H), 1.41 (s, 9H), 0.96 (t, J=8.0 Hz, 9H), 0.73 (q, J=8.0 Hz, 6H). HPLC purity (254 nm): 95.7%.

Example 5: Preparation of N-(2-tert-Butyl-4-(tert-butyldimethylsilyl)-5-hydroxyphenyl)-4-oxo-1,4-dihydroquinoline-3-carboxamide (Compound 5)

A. N-(2-tert-butyl-4-(tert-butyldimethylsilyl)-5-hydroxyphenyl)-4-oxo-1,4-dihydroquinoline-3-carboxamide. To a 20-mL sealed tube purged and maintained with an inert atmosphere of nitrogen, was placed a solution of 2-bromo-4-tert-butyl-5-(4-oxo-1,4-dihydroquinoline-3-carboxamido)phenyl methyl carbonate (300 mg, 0.63 mmol, as prepared in Example 4, Step B) in DMPU (4 mL) dimethyl(propan-2-yl)silane (294 mg, 2.53 mmol), [Rh(cod)$_2$]BF$_4$ (13 mg, 0.03 mmol), and K$_3$PO$_4$ (200 mg, 0.95 mmol) were added. The reaction was stirred for 72 h at 90° C., cooled to rt, and filtered. The filtrate was diluted with 50 mL of water and extracted with EtOAc (3×50 mL). The organic extracts were combined, dried over anhydrous $Na_2SO_4$, and concentrated under reduced pressure. The crude product was purified by Prep-HPLC (HPLC-10: Column, X Bridge C18 OBD Prep Column, 10 μm, 19 mm×250 mm; mobile phase, Water (10 mmol/L $NH_4HCO_3$) and MeCN (60.0% MeCN up to 80.0% in 8 min); Detector, UV 254/220 nm) affording 11.4 mg of the title compound as a white solid. Mass Spectrum (LCMS, ESI pos): Calcd. for $C_{26}H_{35}N_2O_3Si^+$: 451.2 (M+H); Found: 451.3. $^1$H NMR (400 MHz, DMSO-$d_6$): δ 12.89 (s, 1H), 11.91 (s, 1H), 9.20 (s, 1H), 8.87 (s, 1H), 8.33 (d, J=7.2 Hz, 1H), 7.90-7.70 (m, 2H), 7.52 (t, J=7.2 Hz, 1H), 7.27 (s, 1H), 7.19 (s, 1H), 1.39 (s, 9H), 0.90 (s, 9H), 0.26 (s, 9H). HPLC purity (254 nm): 97.2%.

Example 6: Preparation of N-[2-tert-Butyl-4-[dimethyl(propan-2-yl)silyl]-5-hydroxyphenyl]-4-oxo-1,4-dihydroquinoline-3-carboxamide (Compound 6)

A. N-[2-tert-Bbutyl-4-[dimethyl(propan-2-yl)silyl]-5-hydroxyphenyl]-4-oxo-1,4-dihydroquinoline-3-carboxamide. To a 20-mL sealed tube purged and maintained with an inert atmosphere of nitrogen, was placed a solution of 4-tert-butyl-2-iodo-5-(4-oxo-1,4-dihydroquinoline-3-amido)phenyl methyl carbonate (250 mg, 0.48 mmol, as prepared in Example 2, Step D) in DMPU (3 mL) dimethyl(propan-2-yl)silane (196 mg, 1.92 mmol), [Rh(cod)$_2$]BF$_4$ (9.7 mg, 0.02 mmol), and K$_3$PO$_4$ (153 mg, 0.72 mmol) were added. The reaction was stirred for 16 h at 90° C., cooled to rt, and filtered. The filtrate was diluted with 50 mL of water and extracted with EtOAc (3×50 mL). The organic extracts were combined, dried over anhydrous $Na_2SO_4$, and concentrated under reduced pressure. The crude product was purified by Prep-HPLC (HPLC-10: Column, X Bridge C18 OBD Prep Column, 10 μm, 19 mm×250 mm; mobile phase, Water (10 mmol/L $NH_4HCO_3$) and MeCN (65.0% MeCN up to 82.0% in 8 min); Detector, UV 254/220 nm) affording 20.7 mg of the title compound as a gray solid. Mass Spectrum (LCMS, ESI pos): Calcd. for $C_{25}H_{33}N_2O_3Si^+$: 437.2 (M+H); 437.1. $^1$H NMR (300 MHz, DMSO-$d_6$): δ 11.90 (s, 1H), 9.21 (s, 1H), 8.85 (s, 1H), 8.31 (d, J=8.1 Hz, 1H), 7.85-7.70 (m, 2H), 7.49 (t, J=7.8 Hz, 1H), 7.24 (s, 1H), 7.16 (s, 1H), 1.37 (s, 9H), 1.30-0.93 (m, 1H), 0.93 (d, J=7.2 Hz, 6H), 0.18 (s, 6H). HPLC purity (254 nm): 98.9%.

Example 7: N-(2-(tert-Butyl)-4-(dimethyl(phenyl)silyl)-5-hydroxyphenyl)-4-oxo-1,4-dihydroquinoline-3-carboxamide (Compound 7)

A. N-(2-(tert-Butyl)-4-(dimethyl(phenyl)silyl)-5-hydroxyphenyl)-4-oxo-1,4-dihydroquinoline-3-carboxamide. To a 20-mL sealed tube purged and maintained with an inert atmosphere of nitrogen, was placed a solution of 4-tert-butyl-2-iodo-5-(4-oxo-1,4-dihydroquinoline-3-amido)phenyl methyl carbonate (250 mg, 0.48 mmol, as prepared in Example 2, Step D) in DMPU (3 mL), then dimethyl (phenyl)silane (261 mg, 1.92 mmol), [Rh(cod)$_2$]BF$_4$ (9.7 mg, 0.02 mmol), and K$_3$PO$_4$ (153 mg, 0.72 mmol) were added. The reaction was stirred for 16 h at 90° C., cooled to rt and the solids removed by filtration. The filtrate was diluted with water (50 mL) and extracted with EtOAc (3×50 mL). The organic extracts were combined, dried over anhydrous $Na_2SO_4$, and concentrated under reduced pressure. The crude product was purified by Prep-HPLC (Column, X Bridge C18 OBD Prep Column, 10 μm, 19 mm×250 mm; mobile phase, Water (10 mmol/L $NH_4HCO_3$) and ACN (50.0% ACN up to 75.0% in 9 min); Detector, UV 254/220 nm) affording 30.8 mg of the title compound as a gray solid. Mass Spectrum (LCMS, ESI pos): Calcd. for $C_{28}H_{31}N_2O_3Si^+$: 471.2 (M+H); Found: 471.3. $^1$H NMR (400 MHz, DMSO-$d_6$): δ 12.82 (br s, 1H), 11.91 (s, 1H), 9.33 (s, 1H), 8.85 (s, 1H), 8.30 (d, J=8.1 Hz, 1H), 7.81-7.71 (m, 2H), 7.56-7.46 (m, 3H), 7.34 (d, J=2.4 Hz, 3H), 7.18 (s, 1H), 7.13 (s, 1H), 1.30 (s, 9H), 0.50 (s, 6H). HPLC purity (254 nm): 98.9%.

Example 8: Preparation of N-[4-tert-Butyl-5-hydroxy-2-(trimethylsilyl)phenyl]-4-oxo-1,4-dihydroquinoline-3-carboxamide (Compound 8)

A. 4-Bromo-2-tert-butylphenyl methyl carbonate. To a 100-mL 3-necked round-bottom flask purged and maintained with an inert atmosphere of nitrogen, was placed a solution of 4-bromo-2-tert-butylphenol (1 g, 4.36 mmol), TEA (887 mg, 8.77 mmol), and DMAP (54 mg, 0.42 mmol) in DCM (10 mL) then the solution was cooled to 0° C. and methyl chloroformate (494 mg, 5.23 mmol) was added. The reaction was stirred for 3 h at 0° C. then quenched by the addition of 20 mL of water and extracted with DCM (3×20 mL). The organic extracts were combined and concentrated under reduced pressure affording 1.5 g of the title compound as a yellow oil.

B. 4-Bromo-2-tert-butyl-5-nitrophenyl methyl carbonate. To a 50-mL round-bottom flask was placed a solution of 4-bromo-2-tert-butylphenyl methyl carbonate (1.2 g, 4.18 mmol, as prepared in the previous step) in conc. sulfuric acid (5 mL) then the solution was cooled to 0° C. and $KNO_3$ (0.55 g) was added in portions. The reaction was stirred for 2 h at rt then quenched by the addition of 30 mL of water/ice and extracted with DCM (3×30 mL). The organic extracts were combined and concentrated under reduced pressure. The residue was purified by column chromatography eluting with EtOAc/petroleum ether (1:20) affording 1.1 g of the title compound as a yellow solid. $^1$H NMR (300 MHz, $CD_3OD$): δ 7.87 (s, 1H), 7.77 (s, 1H), 3.91 (s, 3H), 1.35 (s, 9H).

C. 5-Amino-4-bromo-2-tert-butylphenyl methyl carbonate. To a 25-mL round-bottom flask was placed a solution of 4-bromo-2-tert-butyl-5-nitrophenyl methyl carbonate (664 mg, 2.00 mmol, as prepared in the previous step) in THF (10 mL) and AcOH (2 mL) then Fe powder (1000 mg, 17.91 mmol) was added in portions over 15 min at 66° C. The reaction was stirred for 8 h at 66° C., cooled to rt, and filtered. The filtrate was concentrated under reduced pressure. The residue was purified by column chromatography eluting with EtOAc/petroleum ether (1:1) affording 450 mg of the title compound as a yellow solid.

D. 4-Bromo-2-tert-butyl-5-(4-oxo-1,4-dihydroquinoline-3-amido)phenyl methyl carbonate. To a 25-mL round-bottom flask was placed a solution of 5-amino-4-bromo-2-tert-butylphenyl methyl carbonate (604 mg, 2.00 mmol, as prepared in the previous step) in DMF (10 mL) then 4-oxo-1,4-dihydroquinoline-3-carboxylic acid (567 mg, 3.00 mmol), DIEA (516 mg, 3.99 mmol), and HATU (1524 mg, 4.00 mmol) were added. The reaction was stirred for 16 h at 65° C. then quenched by the addition of 50 mL of water/ice and extracted with EtOAc (3×25 mL). The organic extracts were combined and concentrated under reduced pressure. The residue was purified by column chromatography eluting with EtOAc/petroleum ether (1:1) affording 800 mg of the title compound as a yellow solid. Mass Spectrum (LCMS, ESI pos): Calcd. for $C_{22}H_{22}BrN_2O_5^+$: 473.1 (M+H); Found: 473.1.

E. N-[4-tert-Butyl-5-hydroxy-2-(trimethylsilyl)phenyl]-4-oxo-1,4-dihydroquinoline-3-carboxamide. To a 40-mL sealed tube was placed a solution of 4-bromo-2-tert-butyl-5-(4-oxo-1,4-dihydroquinoline-3-amido)phenyl methyl carbonate (47.3 mg, 0.10 mmol, as prepared in the previous step) in DMPU (1 mL) then $[Rh(cod)_2]BF_4$ (20.3 mg, 0.05 mmol), hexamethyldisilane (1 mL), and $K_3PO_4$ (84.9 mg, 0.40 mmol) were added under nitrogen. The reaction was stirred for 16 h at 110° C. then quenched by the addition of 10 mL of ice/water and extracted with EtOAc (3×10 mL). The organic extracts were combined, dried over $Na_2SO_4$, and concentrated under reduced pressure. The crude product was purified by Prep-HPLC (HPLC-10: Column, X Bridge Shield RP18 OBD Column, 19*250 mm, 10 um; mobile phase, Water (10 mmol/L $NH_4HCO_3$) and MeCN (60.0% MeCN up to 90.0% in 11 min); Detector, UV 254/220 nm) affording 10.1 mg of the title compound as a white solid. Mass Spectrum (LCMS, ESI pos): Calcd. for $C_{23}H_{29}N_2O_3Si^+$: 409.2 (M+H); Found: 409.2. $^1$H NMR (300 MHz, DMSO-$d_6$): δ 11.73 (s, 1H), 8.96 (s, 1H), 9.51 (s, 1H), 8.43 (s, 1H), 8.30 (d, J=8.4 Hz, 1H), 7.71-7.81 (m, 2H), 7.49 (t, J=8.1 Hz, 1H), 7.29 (s, 1H), 7.21 (s, 1H), 1.34 (s, 9H), 0.28 (s, 9H). HPLC purity (254 nm): 98.1%.

Example 9: Preparation of N-(4-(tert-Butyl)-2-(ethyldimethylsilyl)-5-hydroxyphenyl)-4-oxo-1,4-dihydroquinoline-3-carboxamide (Compound 9)

A. N-(4-(tert-Butyl)-2-(ethyldimethylsilyl)-5-hydroxyphenyl)-4-oxo-1,4-dihydroquinoline-3-carboxamide. To a 40-mL sealed tube purged and maintained with an inert atmosphere of nitrogen, was placed a solution of 4-bromo-2-tert-butyl-5-(4-oxo-1,4-dihydroquinoline-3-amido)phenyl methyl carbonate (47.3 mg, 0.10 mmol, as prepared in Example 8, Step D) in DMPU (0.2 mL), then ethyldimethylsilane (2 mL), $Rh(cod)_2BF_4$ (20 mg), and $K_3PO_4$ (84 mg, 0.40 mmol) were added. The reaction was stirred at 110° C. for 16 h. This reaction was repeated 15 times. The 16 crude reactions were combined, diluted with EtOAc (5 mL), filtered, and concentrated under vacuum. The crude product was purified by Prep-HPLC (Column, XBridge C18 OBD Prep Column, 10 μm, 19 mm×250 mm; mobile phase, Water (10 mmol/L $NH_4HCO_3$) and ACN (70% ACN up to 85% in 11 min); Detector, UV 254/220 nm) affording 20 mg of the title compound as a white solid. Mass Spectrum (LCMS, ESI neg): Calcd. for $C_{24}H_{29}N_2O_3Si^-$: 421.2 (M−H); Found: 421.3. $^1$H NMR (300 MHz, DMSO-$d_6$): δ 12.72 (br s, 1H), 11.71 (s, 1H), 9.52 (s, 1H), 8.84 (s, 1H), 8.30 (d, J=8.4 Hz, 1H), 7.82-7.71 (m, 2H), 7.49 (t, J=8.1 Hz, 1H), 7.28 (s, 1H), 7.20 (s, 1H), 1.34 (s, 9H), 0.95-0.77 (m, 5H), 0.28 (s, 6H). HPLC purity (254 nm): 99.0%.

Example 10: Preparation of N-(4-(tert-Butyl)-2-(tert-butyldimethylsilyl)-5-hydroxyphenyl)-4-oxo-1,4-dihydroquinoline-3-carboxamide (Compound 10)

A. N-(4-(tert-Butyl)-2-(tert-butyldimethylsilyl)-5-hydroxyphenyl)-4-oxo-1,4-dihydroquinoline-3-carboxamide. To a 10-mL sealed tube, was placed a solution of 4-bromo-2-tert-butyl-5-(4-oxo-1,4-dihydroquinoline-3-amido)phenyl methyl carbonate (47.3 mg, 0.10 mmol, as prepared in Example 8, Step D) in DMPU (1 mL), then tert-butyldimethylsilane (0.5 mL), $Rh(cod)_2BF_4$ (20 mg) and $K_3PO_4$ (84 mg, 0.40 mmol) were added under nitrogen. The reaction was stirred for 16 h at 110° C., then diluted with EtOAc (5 mL), filtered, and concentrated under reduced pressure. The crude product was purified by Prep-HPLC (Column, X Bridge C18 OBD Prep Column, 10 μm, 19 mm×250 mm; mobile phase, Water (10 MMOL/L $NH_4HCO_3$) and ACN (83.0% ACN up to 90.0% in 11 min); Detector, UV 254/220 nm) affording 8.9 mg of the title compound as a white solid. Mass Spectrum (LCMS, ESI pos): Calcd. for $C_{26}H_{35}N_2O_3Si^+$: 451.2 (M+H); Found: 451.3. $^1$H NMR (300 MHz, DMSO-$d_6$): δ 12.81 (br s, 1H), 11.43 (s, 1H), 9.54 (s, 1H), 8.82 (s, 1H), 8.29 (d, J=7.8 Hz, 1H), 7.81-7.71

(m, 2H), 7.51-7.46 (m, 1H), 7.22 (s, 1H), 7.05 (s, 1H), 1.34 (s, 9H), 0.86 (s, 9H), 0.25 (s, 6H). HPLC purity (254 nm): 98.2%.

Example 11: Preparation of N-(5-Hydroxy-2,4-bis (trimethylsilyl)phenyl)-4-oxo-1,4-dihydroquinoline-3-carboxamide (Compound 11)

A. N-(2,4-Dibromo-5-hydroxyphenyl)acetamide. To a 3000-mL round-bottom flask was placed a solution of N-(3-hydroxyphenyl)acetamide (15 g, 99.23 mmol) in MeOH (300 mL) and DCM (1.2 L) then Py.Br$_3$ (70.18 g, 220.13 mmol) was added in portions at rt over 1 h. The reaction was stirred overnight at rt then concentrated under reduced pressure. The resulting mixture was diluted with 800 mL of water and extracted with EtOAc (2×1.5 L). The organic extracts were combined, dried over anhydrous Na$_2$SO$_4$, and concentrated under reduced pressure. The residue was purified by column chromatography eluting with EtOAc/petroleum ether (1:1) affording 9 g of the title compound as a white solid. Mass Spectrum (LCMS, ESI pos): Calcd. for $C_8H_8Br_2NO_2^+$: 307.9 (M+H); Found: 308.1.

B. 5-Amino-2,4-dibromophenol. To a 500-mL round-bottom flask was placed a solution of N-(2,4-dibromo-5-hydroxyphenyl)acetamide (10.4 g, 33.66 mmol, as prepared in the previous step) in H$_2$O (130 mL) then conc. HCl (46 mL) was added. The reaction was stirred for 3 h at 100° C. then NaOAc was added to adjust the pH to 7. The solids were removed by filtration then the filtrate was extracted with EtOAc (3×300 mL). The organic extracts were combined, dried over anhydrous Na$_2$SO$_4$, and concentrated under reduced pressure affording 8.2 g of the title compound as a yellow solid. Mass Spectrum (LCMS, ESI pos): Calcd. for $C_6H_6Br_2NO^+$: 265.9 (M+H); Found: 266.2.

C. N-(2,4-Dibromo-5-hydroxyphenyl)-4-oxo-1,4-dihydroquinoline-3-carboxamide. To a 100-mL round-bottom flask was placed a solution of 4-oxo-1,4-dihydroquinoline-3-carboxylic acid (945 mg, 5.00 mmol) in DMF (25 mL) then 5-amino-2,4-dibromophenol (1.99 g, 7.46 mmol, as prepared in the previous step), HATU (3.8 g, 9.99 mmol), and DIEA (2 g, 15.48 mmol) were added. The reaction was stirred for 2 days at 85° C. then diluted with 100 mL of water and extracted with EtOAc (3×200 mL). The organic extracts were combined and concentrated under reduced pressure. The crude product was triturated with EtOAc affording 1.1 g of the title compound as a white solid. Mass Spectrum (LCMS, ESI pos): Calcd. for $C_{16}H_1Br_2N_2O_3^+$: 436.9 (M+H); Found: 437.1.

D. N-[5-Hydroxy-2,4-bis(trimethylsilyl)phenyl]-4-oxo-1,4-dihydroquinoline-3-carboxamide. To a 20-mL sealed tube purged and maintained with an inert atmosphere of nitrogen, was placed a solution of N-(2,4-dibromo-5-hydroxyphenyl)-4-oxo-1,4-dihydroquinoline-3-carboxamide (200 mg, 0.46 mmol, as prepared in the previous step) in DMPU (3 mL) then hexamethyldisilane (533 mg, 3.64 mmol), Pd$_2$(dba)$_3$.CHCl$_3$ (24 mg, 0.02 mmol), JohnPhos (20 mg, 0.07 mmol), and KF/Al$_2$O$_3$ (50%, 265 mg, 4.57 mmol) were added. The reaction was stirred for 16 h at 110° C., cooled to rt, and filtered. The filtrate was diluted with 50 mL of water and extracted with EtOAc (3×50 mL). The organic extracts were combined, dried over anhydrous Na$_2$SO$_4$, and concentrated under reduced pressure. The crude product was purified by Prep-HPLC (HPLC-10: Column, X Bridge C18 OBD Prep Column, 10 μm, 19 mm×250 mm; mobile phase, Water (10 mmol/L NH$_4$HCO$_3$) and MeCN (60.0% MeCN up to 85.0% in 8 min); Detector, UV 254/220 nm) affording 8.2 mg of the title compound as a white solid. Mass Spectrum (LCMS, ESI pos): Calcd. for $C_{22}H_{29}N_2O_3Si_2^+$: 425.2 (M+H); Found: 425.1. $^1$H NMR (400 MHz, DMSO-d$_6$): δ 12.89 (br s, 1H), 11.86 (s, 1H), 9.60 (s, 1H), 8.87 (s, 1H), 8.32 (d, J=8.4 Hz, 1H), 7.90-7.70 (m, 2H), 7.50 (t, J=7.6 Hz, 1H), 7.35 (d, J=7.6 Hz, 2H), 0.31 (s, 9H), 0.25 (s, 9H). HPLC purity (254 nm): 96.1%.

Example 12: Preparation of N-(2-(tert-Butyl)-5-hydroxy-4-(tris(methyl-d$_3$)silyl)phenyl)-4-oxo-1,4-dihydroquinoline-3-carboxamide (Compound 12)

A. N-(2-(tert-Butyl)-5-hydroxy-4-(tris(methyl-d$_3$)silyl)phenyl)-4-oxo-1,4-dihydroquinoline-3-carboxamide. To an 8-mL sealed tube purged and maintained with an inert atmosphere of nitrogen, was placed a solution of 2-bromo-4-tert-butyl-5-(4-oxo-1,4-dihydroquinoline-3-amido)phenyl methyl carbonate (50 mg, 0.11 mmol, as prepared in Example 4, Step B) in DMPU (3 mL) then d$_{18}$-hexamethyldisilane (52 mg, 0.32 mmol), [Rh(cod)$_2$]BF$_4$ (2.2 mg, 0.01 mmol), and K$_3$PO$_4$ (34 mg, 0.16 mmol) were added. The reaction was stirred for 16 h at 90° C., cooled to rt, and filtered. The filtrate was diluted with 50 mL of water and extracted with EtOAc (3×50 mL). The organic extracts were combined, dried over anhydrous Na$_2$SO$_4$, and concentrated under reduced pressure. This reaction was repeated once more then the two batches were combined and purified by Prep-HPLC (HPLC-10: Column, X Bridge C18 OBD Prep Column, 10 μm, 19 mm×250 mm; mobile phase, Water (10 mmol/L NH$_4$HCO$_3$) and MeCN (55.0% MeCN up to 87.0% in 7 min); Detector, UV 254/220 nm) affording 4.9 mg of the title compound as a white solid. Mass Spectrum (LCMS, ESI pos): Calcd. for $C_{23}H_{20}D_9N_2O_3Si^+$: 418.3 (M+H); Found: 418.1. $^1$H NMR (400 MHz, DMSO-d$_6$): δ2.89 (br s, 1H), 11.91 (s, 1H), 9.26 (s, 1H), 8.87 (s, 1H), 8.34-8.32 (m, 1H), 7.90-7.70 (m, 2H), 7.51 (t, J=8.0 Hz, 1H), 7.25 (s, 1H), 7.15 (s, 1H), 1.39 (s, 9H). HPLC purity (254 nm): 95.3%.

Example 13: N-(5-Hydroxy-2,4-bis(tris(methyl-d$_3$) silyl)phenyl)-4-oxo-1,4-dihydroquinoline-3-carboxamide (Compound 13)

A. N-(5-Hydroxy-2,4-bis(tris(methyl-d$_3$)silyl)phenyl)-4-oxo-1,4-dihydroquinoline-3-carboxamide. To a 40-mL sealed tube, purged and maintained with an inert atmosphere of N$_2$, was placed a solution of N-(2,4-dibromo-5-hydroxyphenyl)-4-oxo-1,4-dihydroquinoline-3-carboxamide (50 mg, 0.11 mmol, as prepared in Example 9, Step C) in DMPU (1 mL), then KF/Al$_2$O$_3$ (100 mg, 1.72 mmol), Pd$_2$(dba)$_3$ CHCl$_3$ (20 mg, 0.02 mmol), Johnphos (10 mg, 0.03 mmol) and d$_{18}$-hexamethyldisilane (74 mg, 0.45 mmol) were added. The reaction was stirred for 16 h at 110° C. This step was repeated 5 additional times, then the crude reactions were combined and purified by column chromatography eluting with EtOAc (100%). The resulting material was purified by Prep-HPLC (Column, Atlantis Prep T3 OBD Column, 19*250 mm 10 um; mobile phase, Water (10 mmol/L NH$_4$HCO$_3$) and ACN (75% ACN up to 90% in 8 min); Detector, UV 254/220 nm) affording 27.0 mg of the title compound as a white solid. Mass Spectrum (LCMS, ESI pos): Calcd. for $C_{22}H_{11}D_{18}N_2O_3Si_2^+$: 443.3 (M+H); Found: 443.4. $^1$H NMR (400 MHz, DMSO-d$_6$): δ 12.90 (s, 1H), 11.82 (s, 1H), 9.61 (s, 1H), 8.87 (s, 1H), 8.32 (d, J=8.0 Hz, 1H), 7.85-7.73 (m, 2H), 7.54 (t, J=7.8 Hz, 1H), 7.36 (s, 1H), 7.33 (s, 1H). HPLC purity (254 nm): 95.3%.

Example 14: N-(3-Hydroxy-4-(trimethylsilyl)phenyl)-4-oxo-1,4-dihydroquinoline-3-carboxamide (Compound 17)

A. 5-Nitro-2-(trimethylsilyl)phenol. To a 20-mL sealed tube purged and maintained with an inert atmosphere of nitrogen, was placed a solution of 2-bromo-5-nitrophenol (1.1 g, 5.05 mmol) in DMPU (10 mL) then hexamethyldisilane (14.7 g, 100.42 mmol), Pd$_2$(dba)$_3$CHCl$_3$ (520 mg, 0.50 mmol), JohnPhos (450 mg, 1.51 mmol), and KF (1.45 g, 25.00 mmol) were added. The reaction was stirred at 110° C. for 16 h in an oil bath, then cooled to rt and filtered. The filtrate was diluted with water (100 mL), and extracted with EtOAc (3×100 mL). The organic extracts were combined, dried over anhydrous Na$_2$SO$_4$, and concentrated under reduced pressure. The residue was purified by column chromatography eluting with EtOAc/petroleum ether (0-50%) affording 850 mg of as yellow oil. Mass Spectrum (LCMS, ESI neg): Calcd. for C$_9$H$_{12}$NO$_3$Si$^-$: 210.1 (M−H); Found: 210.0.

B. 5-Amino-2-(trimethylsilyl)phenol. To a 50-mL round-bottom flask, was placed a solution of 5-nitro-2-(trimethylsilyl)phenol (200 mg, 0.95 mmol, as prepared in the previous step) in methanol/THF (4/2 mL) then Ni(OAc)$_2$ (168 mg, 0.95 mmol) was added followed by NaBH$_4$ (36 mg, 0.95 mmol), in portions at 0° C. The reaction was stirred at 0° C. for 10 min in a water/ice bath then the solids were removed by filtration. The reaction was quenched by the addition of water (50 mL) and the resulting solution was extracted with EtOAc (3×50 mL). The organic layers were combined, dried over anhydrous Na$_2$SO$_4$, and diluted with DMF (6 mL). The resulting solution was concentrated under reduced pressure to remove EtOAc affording a DMF solution of the title compound, which was used directly in the next step without isolation. Mass Spectrum (LCMS, ESI pos): Calcd. for C$_9$H$_{16}$NOSi$^+$: 182.1 (M+H); Found: 182.1.

C. N-(3-Hydroxy-4-(trimethylsilyl)phenyl)-4-oxo-1,4-dihydroquinoline-3-carboxamide. To a 50-mL round-bottom flask purged and maintained with an inert atmosphere of nitrogen, was placed a solution of 5-amino-2-(trimethylsilyl) phenol as in DMF (6 mL, as prepared in the previous step), then 4-oxo-1,4-dihydroquinoline-3-carboxylic acid (180 mg, 0.95 mmol), HATU (543 mg, 1.43 mmol), and DIEA (245 mg, 1.90 mmol) were added. The reaction was stirred at rt for 16 h, then diluted with water (50 mL) and extracted with EtOAc (2×50 mL). The organic extracts were combined, dried over anhydrous Na$_2$SO$_4$, and concentrated under reduced pressure. The crude product was purified by re-crystallization from EtOAc affording 59.4 mg of the title compound as a white solid. Mass Spectrum (LCMS, ESI pos): Calcd. for C$_{19}$H$_{21}$N$_2$O$_3$Si$^+$: 353.1 (M+H); Found: 353.3. $^1$H NMR (300 MHz, DMSO-d$_6$): δ 12.95 (s, 1H), 12.41 (s, 1H), 9.51 (s, 1H), 8.86 (s, 1H), 8.32 (d, J=7.5 Hz, 1H), 7.82-7.74 (m, 2H), 7.54 (t, J=7.5 Hz, 1H), 7.39 (s, 1H), 7.19 (d, J=7.8 Hz, 1H), 7.02-7.69 (m, 1H), 0.23 (s, 9H). HPLC purity (254 nm): 99.2%.

Example 15: N-(3-Hydroxy-4-(trimethylsilyl)phenyl)-4-oxo-1,4-dihydroquinoline-3-carboxamide (Compound 18)

A. 2-Bromo-4-fluorophenyl methyl carbonate. To a 100-mL round-bottom flask was placed a solution of 2-bromo-4-fluorophenol (1.9 g, 9.95 mmol) in DCM (20 mL) then TEA (2.0 g, 19.76 mmol) and DMAP (120 mg, 0.98 mmol) were added, followed by the dropwise addition of methyl chloroformate (1.23 g, 13.02 mmol) with stirring at 0° C. The reaction was stirred at rt for 3 h, then quenched by the addition of water (100 mL) and extracted with DCM (3×100 mL). The organic extracts were combined, dried over anhydrous Na$_2$SO$_4$, and concentrated under reduced pressure affording 1.5 g of the title compound as a yellow oil.

B. 2-Bromo-4-fluoro-5-nitrophenyl methyl carbonate. To a 100-mL round-bottom flask, was placed a solution of 2-bromo-4-fluorophenyl methyl carbonate (1 g, 4.02 mmol, as prepared in the previous step) in DCM (10 mL), then HNO$_3$/H$_2$SO$_4$ (1:1) (5 mL) was added dropwise with stirring at 0° C. The reaction was stirred at rt for 2 h, then poured into 200 mL of water/ice and extracted with DCM (3×100 mL). The organic extracts were combined, dried over anhydrous Na$_2$SO$_4$, and concentrated under reduced pressure. The residue was purified by column chromatography eluting with EtOAc/petroleum ether (2:1) affording 700 mg of the title compound as a light yellow solid. Mass Spectrum (LCMS, ESI pos): Calcd. for C$_8$H$_6$BrFNO$_5$$^+$: 293.9 (M+H); Found: 294.0.

C. 4-Fluoro-5-nitro-2-(trimethylsilyl)phenol. To a 20-mL sealed tube purged and maintained with an inert atmosphere of nitrogen, was placed a solution of 2-bromo-4-fluoro-5-nitrophenyl methyl carbonate (300 mg, 1.02 mmol, as prepared in the previous step) in DMPU (3 mL) then hexamethyldisilane (2.98 g, 20.36 mmol), PdCl$_2$ (184 mg, 1.04 mmol), and K$_3$PO$_4$ (441 mg, 2.08 mmol) were added. The reaction was stirred at 110° C. for 24 h in an oil bath, then cooled to rt and filtered. The filtrate was diluted with water (50 mL) and extracted with EtOAc (3×100 mL). The organic extracts were combined, dried over anhydrous Na$_2$SO$_4$, and concentrated under reduced pressure. The residue was purified by column chromatography eluting with EtOAc/petroleum ether (0-60%) affording 150 mg of the title compound as a yellow oil. Mass Spectrum (LCMS, ESI neg): Calcd. for C$_9$H$_{11}$FNO$_3$Si$^-$: 228.1 (M+H); Found: 228.0.

D. 5-Amino-4-fluoro-2-(trimethylsilyl)phenol. To a 50-mL round-bottom flask was placed a solution of 4-fluoro-5-nitro-2-(trimethylsilyl)phenol (150 mg, 0.65 mmol, as prepared in the previous step) in methanol/THF (2/2 mL), then Ni(OAc)$_2$ (116 mg, 0.66 mmol) was added followed by the addition of NaBH$_4$ (25 mg, 0.66 mmol) in portions at 0° C. The reaction was stirred at 0° C. for 10 min then the solids were removed by filtration. The filtrate was diluted with water (20 mL) and extracted with EtOAc (3×20 mL). The organic extracts were combined, dried over anhydrous Na$_2$SO$_4$, and concentrated under reduced pressure affording 100 mg of the title compound as a yellow oil. Mass Spectrum (LCMS, ESI pos): Calcd. for C$_9$H$_{15}$FNOSi$^+$: 200.1 (M+H); Found: 200.1.

E. N-(3-Hydroxy-4-(trimethylsilyl)phenyl)-4-oxo-1,4-dihydroquinoline-3-carboxamide. To a 50-mL round-bottom flask was placed a solution of 5-amino-4-fluoro-2-(trimethylsilyl)phenol (100 mg, 0.50 mmol, as prepared in the previous step) in DMF (5 mL) then 4-oxo-1,4-dihydroquinoline-3-carboxylic acid (95 mg, 0.50 mmol), HATU (285 mg, 0.75 mmol), and DIEA (129 mg, 1.00 mmol) were added. The reaction was stirred at rt for 16 h, then diluted with water (50 mL) and extracted with EtOAc (3×50 mL). The organic extracts were combined, dried over anhydrous Na$_2$SO$_4$, and concentrated under reduced pressure. The crude product was purified by Prep-HPLC (Column, X Bridge C18 OBD Prep Column, 10 μm, 19 mm×250 mm; mobile phase, Water (10 mM NH$_4$HCO$_3$) and ACN (50.0% ACN up to 83.0% in 8 min); Detector, UV 254/220 nm) affording 68.2 mg of the title compound as an off-white solid. Mass Spectrum (LCMS, ESI pos): Calcd. for C$_{19}$H$_{20}$FN$_2$O$_3$Si$^+$: 371.1 (M+H); Found: 371.1. $^1$H NMR (400 MHz, DMSO-d$_6$): δ 12.97 (s, 1H), 12.69 (d, J=2.4 Hz, 1H), 9.48 (s, 1H), 8.88 (s, 1H), 8.35-8.32 (m, 1H), 8.08 (d, J=6.0 Hz, 1H), 7.85-7.75 (m, 2H), 7.56-7.52 (m, 1H), 7.03 (d, J=10.8 Hz, 1H), 0.24 (s, 9H). HPLC purity (254 nm): 99.1%.

Example 16: N-(5-Hydroxy-2-(trifluoromethyl)-4-(trimethylsilyl)phenyl)-4-oxo-1,4-dihydroquinoline-3-carboxamide (Compound 19)

A. 2-Bromo-4-(trifluoromethyl)phenyl methyl carbonate. To a 250-mL round-bottom flask was placed a solution of 2-bromo-4-(trifluoromethyl)phenol (4.8 g, 19.92 mmol) in DCM (100 mL) then TEA (4 g, 39.53 mmol) and DMAP (250 mg, 2.05 mmol) were added, followed by the dropwise addition of methyl chloroformate (3.8 g, 40.21 mmol) with stirring at 0° C. The reaction was stirred at rt for 3 h then quenched by the addition of water (100 mL) and extracted with DCM (3×100 mL). The organic extracts were combined, dried over anhydrous $Na_2SO_4$, and concentrated under reduced pressure. The residue was purified by column chromatography eluting with EtOAc/petroleum ether (0-5%) affording 4.0 g of the title compound as yellow oil.

B. 2-Bromo-5-nitro-4-(trifluoromethyl)phenyl methyl carbonate. To a 250-mL round-bottom flask was placed a solution of 2-bromo-4-(trifluoromethyl)phenyl methyl carbonate (4 g, 13.38 mmol, as prepared in the previous step) in $H_2SO_4$ (20 mL) then $HNO_3/H_2SO_4$ (1:1, 10 mL) was added dropwise with stirring at 0° C. The reaction was stirred at rt for 3 h then quenched by the addition of 300 mL of water/ice and extracted with DCM (3×100 mL). The organic extracts were combined, dried over anhydrous $Na_2SO_4$, and concentrated under reduced pressure. The residue was purified by column chromatography eluting with EtOAc/petroleum ether (0-50%) affording 1.0 g of the title compound as a light yellow solid.

C. 5-Nitro-4-(trifluoromethyl)-2-(trimethylsilyl)phenol. To a 40-mL sealed tube purged and maintained with an inert atmosphere of nitrogen, was placed a solution of 2-bromo-5-nitro-4-(trifluoromethyl)phenyl methyl carbonate (300 mg, 0.87 mmol, as prepared in the previous step) in DMPU (3 mL) then hexamethyldisilane (2.6 g, 17.76 mmol), $PdCl_2$ (154 mg, 0.87 mmol), and $K_3PO_4$ (369 mg, 1.74 mmol) were added. The reaction was stirred at 110° C. for 24 h, then cooled and filtered. The filtrate was diluted with water (50 mL) and extracted with EtOAc (3×100 mL). The organic extracts were combined, dried over anhydrous $Na_2SO_4$, and concentrated under reduced pressure. The residue was purified by column chromatography eluting with EtOAc/petroleum ether (0-50%) affording 160 mg of the title compound as light yellow oil. Mass Spectrum (LCMS, ESI neg): Calcd. for $C_{10}H_{11}F_3NO_3Si^-$: 278.0 (M+H); Found: 278.0.

D. 5-Amino-4-(trifluoromethyl)-2-(trimethylsilyl)phenol. To a 25-mL round-bottom flask was placed a solution of 5-nitro-4-(trifluoromethyl)-2-(trimethylsilyl)phenol (160 mg, 0.57 mmol, as prepared in the previous step) and $Ni(OAc)_2$ (102 mg, 0.58 mmol) in methanol/THF (2 mL), then $NaBH_4$ (22 mg, 0.58 mmol) was added in portions at 0° C. The reaction was stirred at 0° C. for 10 min, then filtered, diluted with water (100 mL), and extracted with EtOAc (3×100 mL). The organic extracts were combined, dried over anhydrous $Na_2SO_4$, and concentrated under reduced pressure affording 120 mg of the title compound as a yellow oil. Mass Spectrum (LCMS, ESI pos): Calcd. for $C_{10}H_{15}F_3NOSi^+$: 250.1 (M+H); Found: 250.1.

E. N-(5-Hydroxy-2-(trifluoromethyl)-4-(trimethylsilyl)phenyl)-4-oxo-1,4-dihydroquinoline-3-carboxamide. To a 100-mL round-bottom flask was placed a solution of 5-amino-4-(trifluoromethyl)-2-(trimethylsilyl)phenol (120 mg, 0.48 mmol, as prepared in the previous step) in DMF (10 mL), then 4-oxo-1,4-dihydroquinoline-3-carboxylic acid (137 mg, 0.72 mmol), HATU (365 mg, 0.96 mmol), and DIEA (186 mg, 1.44 mmol) were added. The reaction was stirred at rt for 16 h, diluted with water (100 mL), and extracted with EtOAc (3×100 mL). The organic extracts were combined, dried over anhydrous $Na_2SO_4$, and concentrated under reduced pressure. The residue was purified by Chiral-Prep-HPLC (Column, Chiralpak IA, 2*25 cm, 5 um; mobile phase, Hex- and ethanol-(hold 10.0% ethanol-in 13 min); Detector, UV 220/254 nm) affording in 6.6 mg of the title compound as a white solid. Mass Spectrum (LCMS, ESI pos): Calcd. for $C_{20}H_{20}F_3N_2O_3Si^+$: 421.1 (M+H); Found: 421.2. $^1$H NMR (300 MHz, DMSO-$d_6$): δ 13.15 (br s, 1H), 12.67 (s, 1H), 10.37 (s, 1H), 8.86 (s, 1H), 8.31 (d, J=8.1 Hz, 1H), 7.99 (s, 1H), 7.84-7.73 (m, 2H), 7.54-7.49 (m, 1H), 7.45 (s, 1H), 0.25 (s, 9H). HPLC purity (254 nm): 99.8%.

Exemplary compounds of the disclosure prepared by the above synthetic procedures are provided in Table 1:

TABLE 1

| Compound | Structure | Name |
| --- | --- | --- |
| 1 | 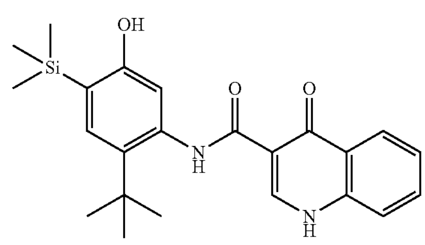 | N-(2-(tert-Buty)-5-hydroxy-4-(trimethylsilyl)phenyl)-4-oxo-1,4-dihydroquinoline-3-carboxamide |
| 2 | 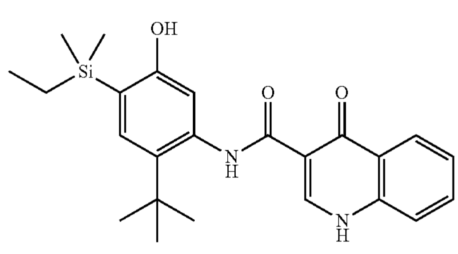 [SMILES: CC[Si](C)(C)c1cc(C(C)(C)C)c(NC(=O)c2c[nH]c3ccccc3c2=O)cc1O] | N-(2-(tert-Butyl)-4-(ethyldimethylsilyl)-5-hydroxyphenyl)-4-oxo-1,4-dihydroquinoline-3-carboxamide |

TABLE 1-continued

| Compound | Structure | Name |
|---|---|---|
| 3 | 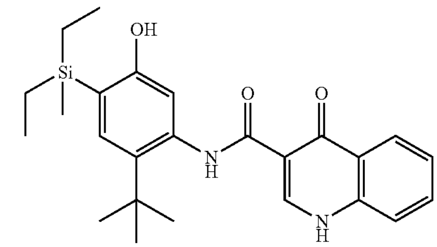 [SMILES: CC[Si](C)(CC)c1cc(C(C)(C)C)c(NC(=O)c2c[nH]c3ccccc3c2=O)cc1O] | N-(2-(tert-Butyl)-4-(diethyl(methyl)silyl)-5-hydroxyphenyl)-4-oxo-1,4-dihydroquinoline-3-carboxamide |
| 4 | 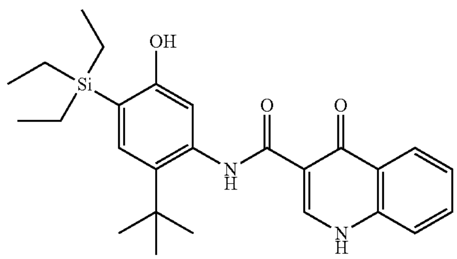 [SMILES: CC[Si](CC)(CC)c1cc(C(C)(C)C)c(NC(=O)c2c[nH]c3ccccc3c2=O)cc1O] | N-(2-(tert-Butyl)-5-hydroxy-4-(triethylsilyl)phenyl)-4-oxo-1,4-dihydroquinoline-3-carboxamide |
| 5 | 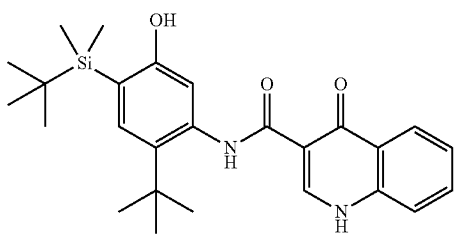 [SMILES: CC(C)(C)c1cc([Si](C)(C)C(C)(C)C)c(O)cc1NC(=O)c1c[nH]c2ccccc2c1=O] | N-(2-(tert-Butyl)-4-(tert-butyldimethylsilyl)-5-hydroxyphenyl)-4-oxo-1,4-dihydroquinoline-3-carboxamide |
| 6 | 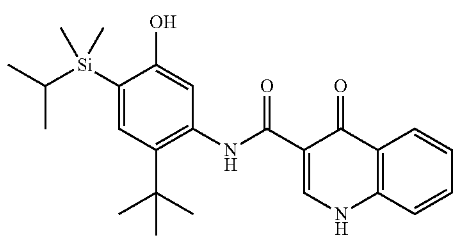 [SMILES: CC(C)[Si](C)(C)c1cc(C(C)(C)C)c(NC(=O)c2c[nH]c3ccccc3c2=O)cc1O] | N-(2-(tert-Butyl)-5-hydroxy-4-(isopropyldimethylsilyl)phenyl)-4-oxo-1,4-dihydroquinoline-3-carboxamide |
| 7 | 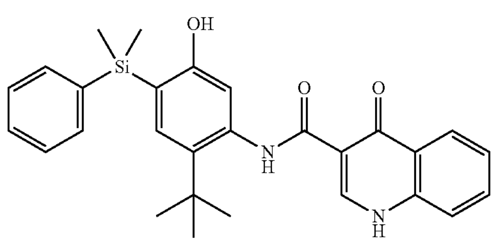 [SMILES: CC(C)(C)c1cc([Si](C)(C)c2ccccc2)c(O)cc1NC(=O)c1c[nH]c2ccccc2c1=O] | N-(2-(tert-Butyl)-4-(dimethyl(phenyl)silyl)-5-hydroxyphenyl)-4-oxo-1,4-dihydroquinoline-3-carboxamide |
| 8 | 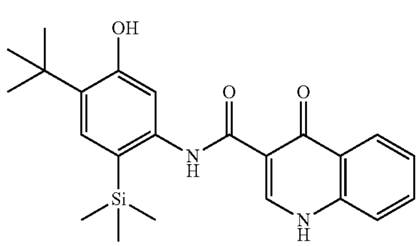 [SMILES: CC(C)(C)c1cc([Si](C)(C)C)c(NC(=O)c2c[nH]c3ccccc3c2=O)cc1O] | N-(4-(tert-Butyl)-5-hydroxy-2-(trimethylsilyl)phenyl)-4-oxo-1,4-dihydroquinoline-3-carboxamide |

TABLE 1-continued

| Compound | Structure | Name |
|---|---|---|
| 9 | 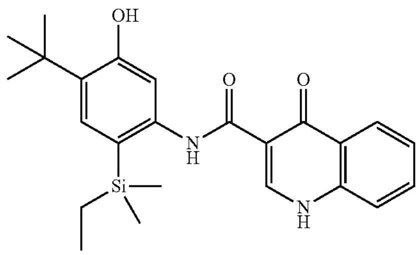 [SMILES: CC[Si](C)(C)c1cc(C(C)(C)C)c(O)cc1NC(=O)c1c[nH]c2ccccc2c1=O] | N-(4-(tert-Butyl)-2-(ethyldimethylsilyl)-5-hydroxyphenyl)-4-oxo-1,4-dihydroquinoline-3-carboxamide |
| 10 | 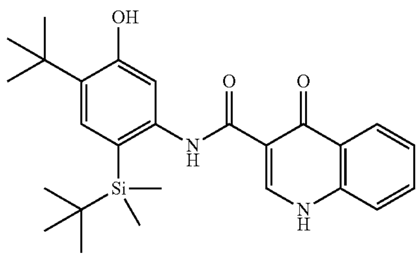 [SMILES: CC(C)(C)c1cc([Si](C)(C)C(C)(C)C)c(NC(=O)c2c[nH]c3ccccc3c2=O)cc1O] | N-(4-(tert-Butyl)-2-(tert-butyldimethylsilyl)-5-hydroxyphenyl)-4-oxo-1,4-dihydroquinoline-3-carboxamide |
| 11 | 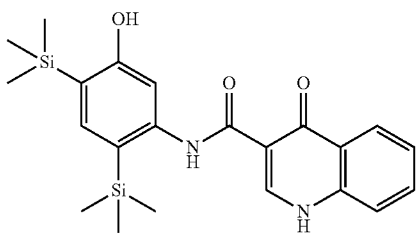 [SMILES: C[Si](C)(C)c1cc([Si](C)(C)C)c(NC(=O)c2c[nH]c3ccccc3c2=O)cc1O] | N-(5-Hydroxy-2,4-bis(trimethylsilyl)phenyl)-4-oxo-1,4-dihydroquinoline-3-carboxamide |
| 12 | 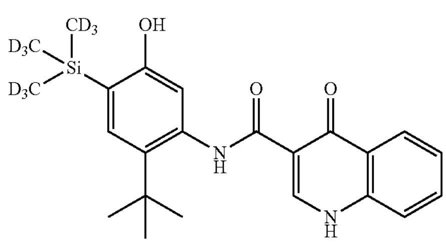 [SMILES: [2H]C([2H])([2H])[Si](c1cc(C(C)(C)C)c(NC(=O)c2c[nH]c3ccccc3c2=O)cc1O)(C([2H])([2H])[2H])C([2H])([2H])[2H]] | N-(2-(tert-Butyl)-5-hydroxy-4-(tris(methyl-d3)silyl)phenyl)-4-oxo-1,4-dihydroquinoline-3-carboxamide |
| 13 | 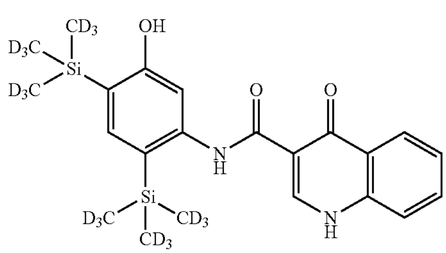 [SMILES: [2H]C([2H])([2H])[Si](c1cc([Si](C([2H])([2H])[2H])(C([2H])([2H])[2H])C([2H])([2H])[2H])c(NC(=O)c2c[nH]c3ccccc3c2=O)cc1O)(C([2H])([2H])[2H])C([2H])([2H])[2H]] | N-(5-Hydroxy-2,4-bis(tris(methyl-d3)silyl)phenyl)-4-oxo-1,4-dihydroquinoline-3-carboxamide |
| 14 | 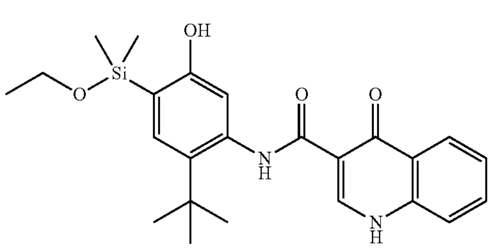 [SMILES: CCO[Si](C)(C)c1cc(C(C)(C)C)c(NC(=O)c2c[nH]c3ccccc3c2=O)cc1O] | N-(2-(tert-Butyl)-4-(ethoxydimethylsilyl)-5-hydroxyphenyl)-4-oxo-1,4-dihydroquinoline-3-carboxamide |

TABLE 1-continued

| Compound | Structure | Name |
|---|---|---|
| 15 | 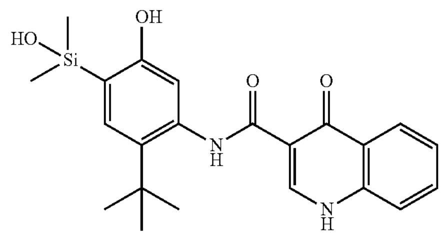 [SMILES: CC(C)(C)c1cc([Si](C)(C)O)c(O)cc1NC(=O)c1c[nH]c2ccccc2c1=O] | N-(2-(tert-Butyl)-5-hydroxy-4-(hydroxydimethylsilyl)phenyl)-4-oxo-1,4-dihydroquinoline-3-carboxamide |
| 16 | 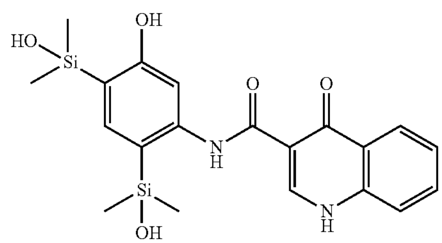 [SMILES: C[Si](C)(O)c1cc([Si](C)(C)O)c(NC(=O)c2c[nH]c3ccccc3c2=O)cc1O] | N-(5-Hydroxy-2,4-bis(hydroxydimethylsilyl)phenyl)-4-oxo-1,4-dihydroquinoline-3-carboxamide |
| 17 | 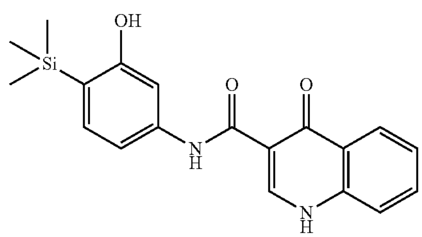 [SMILES: C[Si](C)(C)c1ccc(NC(=O)c2c[nH]c3ccccc3c2=O)cc1O] | N-(3-Hydroxy-4-(trimethylsilyl)phenyl)-4-oxo-1,4-dihydroquinoline-3-carboxamide |
| 18 | 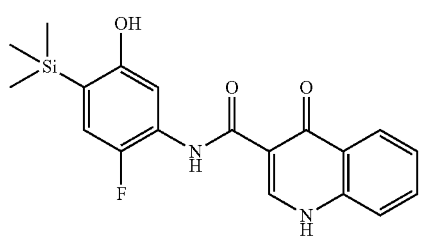 [SMILES: C[Si](C)(C)c1cc(F)c(NC(=O)c2c[nH]c3ccccc3c2=O)cc1O] | N-(2-Fluoro-5-hydroxy-4-(trimethylsilyl)phenyl)-4-oxo-1,4-dihydroquinoline-3-carboxamide |
| 19 | 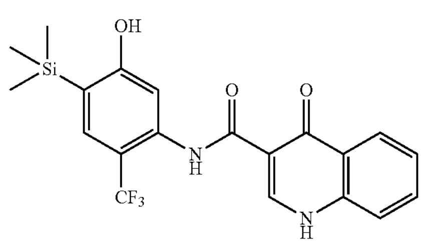 [SMILES: C[Si](C)(C)c1cc(C(F)(F)F)c(NC(=O)c2c[nH]c3ccccc3c2=O)cc1O] | N-(5-Hydroxy-2-(trifluoromethyl)-4-(trimethylsilyl)phenyl)-4-oxo-1,4-dihydroquinoline-3-carboxamide |
| 20 | 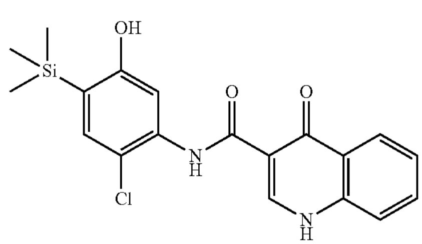 [SMILES: C[Si](C)(C)c1cc(Cl)c(NC(=O)c2c[nH]c3ccccc3c2=O)cc1O] | N-(2-Chloro-5-hydroxy-4-(trimethylsilyl)phenyl)-4-oxo-1,4-dihydroquinoline-3-carboxamide |

TABLE 1-continued

| Compound | Structure | Name |
|---|---|---|
| 21 | 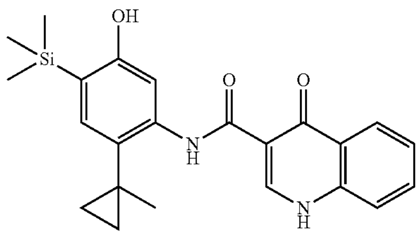 [SMILES: CC1(c2cc([Si](C)(C)C)c(O)cc2NC(=O)c2c[nH]c3ccccc3c2=O)CC1] | N-(5-Hydroxy-2-(1-methylcyclopropyl)-4-(trimethylsilyl)phenyl)-4-oxo-1,4-dihydroquinoline-3-carboxamide |
| 22 | 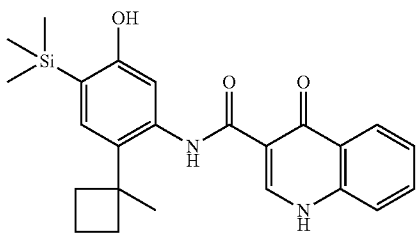 [SMILES: CC1(c2cc([Si](C)(C)C)c(O)cc2NC(=O)c2c[nH]c3ccccc3c2=O)CCC1] | N-(5-Hydroxy-2-(1-methylcyclobutyl)-4-(trimethylsilyl)phenyl)-4-oxo-1,4-dihydroquinoline-3-carboxamide |
| 23 | 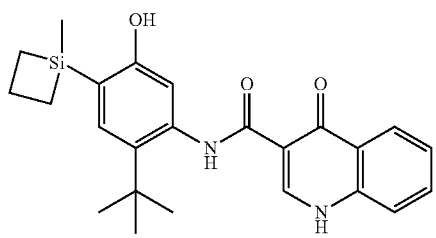 [SMILES: CC(C)(C)c1cc([Si]2(C)CCC2)c(O)cc1NC(=O)c1c[nH]c2ccccc2c1=O] | N-(2-(tert-Butyl)-5-hydroxy-4-(1-methylsiletan-1-yl)phenyl)-4-oxo-1,4-dihydroquinoline-3-carboxamide |
| 24 | 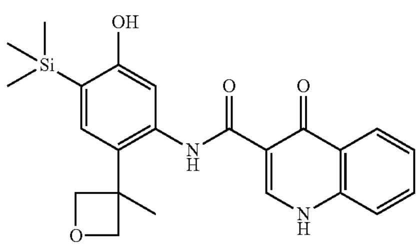 [SMILES: CC1(c2cc([Si](C)(C)C)c(O)cc2NC(=O)c2c[nH]c3ccccc3c2=O)COC1] | N-(5-Hydroxy-2-(3-methyloxetan-3-yl)-4-(trimethylsilyl)phenyl)-4-oxo-1,4-dihydroquinoline-3-carboxamide |
| 25 | 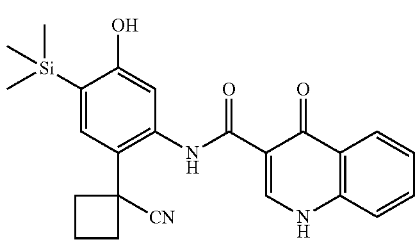 [SMILES: C[Si](C)(C)c1cc(C2(C#N)CCC2)c(NC(=O)c2c[nH]c3ccccc3c2=O)cc1O] | N-(2-(1-Cyanocyclobutyl)-5-hydroxy-4-(trimethylsilyl)phenyl)-4-oxo-1,4-dihydroquinoline-3-carboxamide |
| 26 | 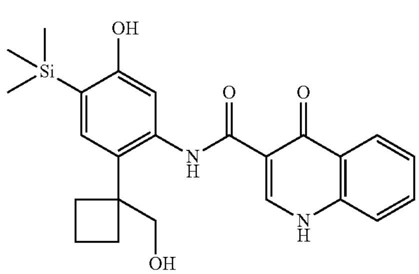 [SMILES: C[Si](C)(C)c1cc(C2(CO)CCC2)c(NC(=O)c2c[nH]c3ccccc3c2=O)cc1O] | N-(5-Hydroxy-2-(1-(hydroxymethyl)cyclobutyl)-4-(trimethylsilyl)phenyl)-4-oxo-1,4-dihydroquinoline-3-carboxamide |

TABLE 1-continued

| Compound | Structure | Name |
|---|---|---|
| 27 | 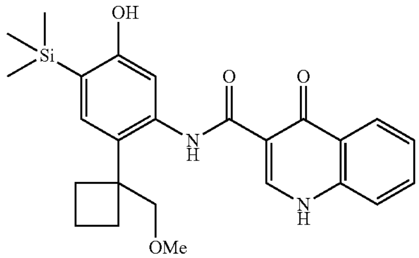 [SMILES: COCC1(c2cc([Si](C)(C)C)c(O)cc2NC(=O)c2c[nH]c3ccccc3c2=O)CCC1] | N-(5-Hydroxy-2-(1-(methoxymethyl)cyclobutyl)-4-(trimethylsilyl)phenyl)-4-oxo-1,4-dihydroquinoline-3-carboxamide |
| 28 | 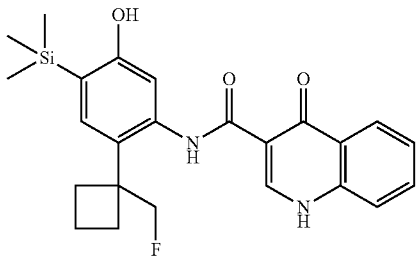 [SMILES: C[Si](C)(C)c1cc(C2(CF)CCC2)c(NC(=O)c2c[nH]c3ccccc3c2=O)cc1O] | N-(2-(1-(Fluoromethyl)cyclobutyl)-5-hydroxy-4-(trimethylsilyl)phenyl)-4-oxo-1,4-dihydroquinoline-3-carboxamide |

Example 17: CFTR Activity Assays i. Ussing Measurements

As discussed above, Ussing measurements are used to measure CFTR activity. In this method, primary lung epithelial cells (hBEs) homozygous for the Cystic Fibrosis-causing ΔF508 mutation are differentiated for a minimum of 4 weeks in an air-liquid interface on SnapWell filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages are stabilized, the chambers are clamped, and data is recorded by pulse readings every 5 seconds. Following baseline current stabilization, the following additions can be applied and the changes in current and resistance of the cells can be monitored:

1. Benzamil to the apical chamber to inhibit ENaC sodium channel.
2. Forskolin to both chambers to activate ΔF508-CFTR by phosphorylation.
3. VX-770 to the apical chamber to potentiate ΔF508-CFTR channel opening.
4. CFTRinh-172 to the apical chamber to inhibit ΔF508-CFTR Cl— conductance.

The inhibitable current (that current that is blocked by CFTRinh-172) is measured as the specific activity of the ΔF508-CFTR channel, and increases in response to compound in this activity over that observed in vehicle-treated samples are identified as the correction of ΔF508-CFTR function imparted by the compound tested.

The results are shown below in Table 2. (+ indicates activity <200% of a corrector (VX-809 (3 uM)) with compound at 1 uM; ++ indicates activity >200% of a corrector (VX-809 (3 uM)) with compound at 1 uM.

TABLE 2

| Compound | Structure | Activity |
|---|---|---|
| 1 | 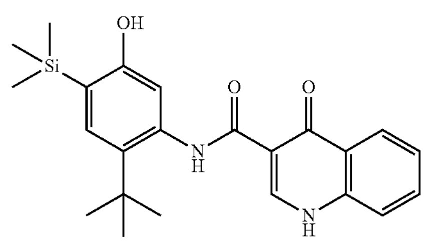 [SMILES: CC(C)(C)c1cc([Si](C)(C)C)c(O)cc1NC(=O)c1c[nH]c2ccccc2c1=O] | ++ |

TABLE 2-continued

| Compound | Structure | Activity |
|---|---|---|
| 2 | (structure) | ++ |
| 3 | (structure) | ++ |
| 4 | (structure) | + |
| 5 | (structure) | ++ |
| 6 | (structure) | ++ |
| 7 | (structure) | ++ |

TABLE 2-continued

| Compound | Structure | Activity |
|---|---|---|
| 8 | 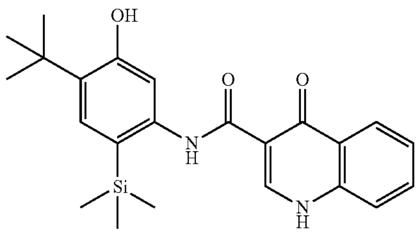 | ++ |
| 9 | 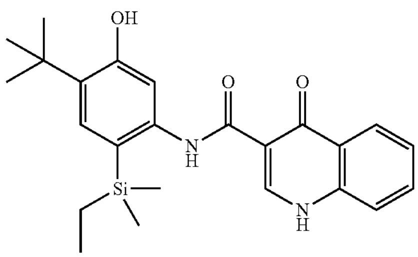 [SMILES: CC[Si](C)(C)c1cc(C(C)(C)C)c(O)cc1NC(=O)c1c[nH]c2ccccc2c1=O] | |
| 10 | 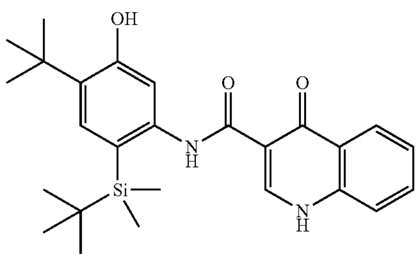 [SMILES: CC(C)(C)c1cc([Si](C)(C)C(C)(C)C)c(NC(=O)c2c[nH]c3ccccc3c2=O)cc1O] | ++ |
| 11 | 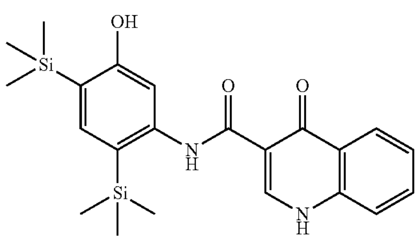 [SMILES: C[Si](C)(C)c1cc([Si](C)(C)C)c(NC(=O)c2c[nH]c3ccccc3c2=O)cc1O] | ++ |
| 12 | 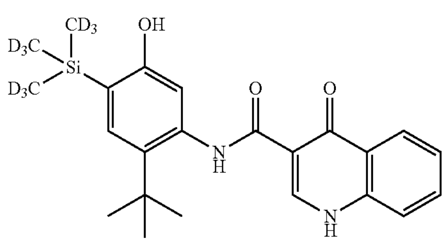 [SMILES: [2H]C([2H])([2H])[Si](c1cc(C(C)(C)C)c(NC(=O)c2c[nH]c3ccccc3c2=O)cc1O)(C([2H])([2H])[2H])C([2H])([2H])[2H]] | ++ |
| 13 | 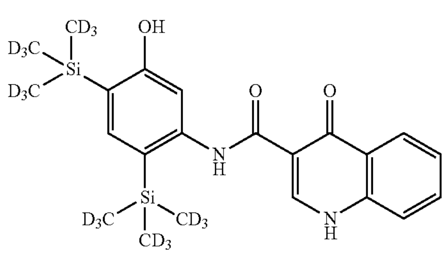 [SMILES: [2H]C([2H])([2H])[Si](c1cc([Si](C([2H])([2H])[2H])(C([2H])([2H])[2H])C([2H])([2H])[2H])c(NC(=O)c2c[nH]c3ccccc3c2=O)cc1O)(C([2H])([2H])[2H])C([2H])([2H])[2H]] | ++ |

TABLE 2-continued

| Compound | Structure | Activity |
|---|---|---|
| 14 | (structure) | |
| 15 | (structure) | |
| 16 | (structure) | |
| 17 | (structure) | ++ |
| 18 | (structure) | ++ |
| 19 | (structure) | ++ |

TABLE 2-continued

| Compound | Structure | Activity |
|---|---|---|
| 20 | 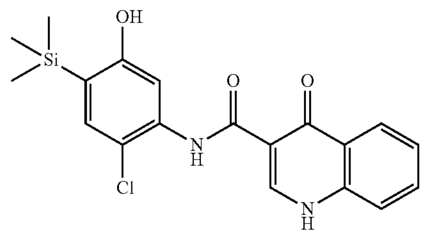 [SMILES: C[Si](C)(C)c1cc(Cl)c(NC(=O)c2c[nH]c3ccccc3c2=O)cc1O] | |
| 21 | 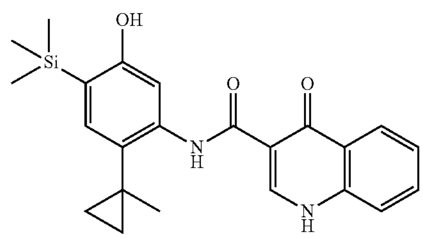 [SMILES: CC1(c2cc([Si](C)(C)C)c(O)cc2NC(=O)c2c[nH]c3ccccc3c2=O)CC1] | |
| 22 | 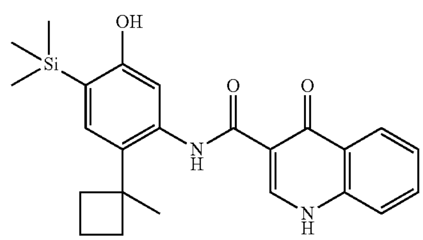 [SMILES: CC1(c2cc([Si](C)(C)C)c(O)cc2NC(=O)c2c[nH]c3ccccc3c2=O)CCC1] | |
| 23 | 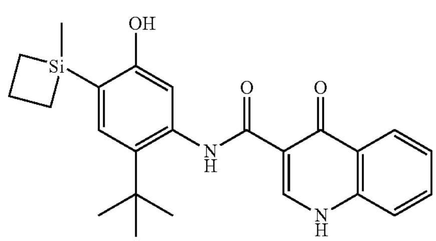 [SMILES: CC(C)(C)c1cc([Si]2(C)CCC2)c(O)cc1NC(=O)c1c[nH]c2ccccc2c1=O] | |
| 24 | 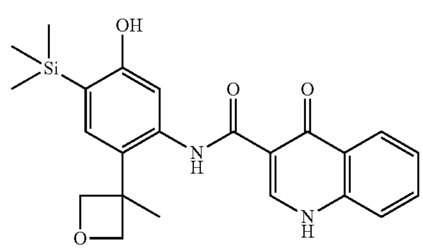 [SMILES: CC1(c2cc([Si](C)(C)C)c(O)cc2NC(=O)c2c[nH]c3ccccc3c2=O)COC1] | |
| 25 | 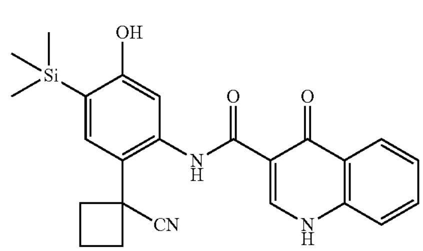 [SMILES: C[Si](C)(C)c1cc(C2(C#N)CCC2)c(NC(=O)c2c[nH]c3ccccc3c2=O)cc1O] | |

TABLE 2-continued

| Compound | Structure | Activity |
|---|---|---|
| 26 | 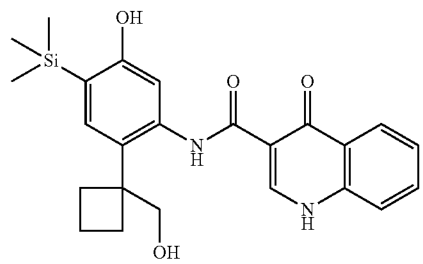 [SMILES: C[Si](C)(C)c1cc(C2(CO)CCC2)c(NC(=O)c2c[nH]c3ccccc3c2=O)cc1O] | |
| 27 | 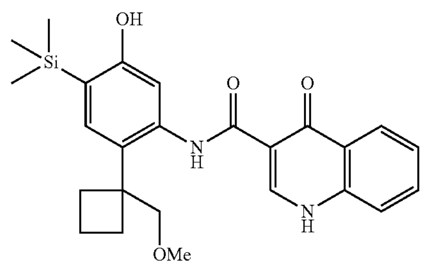 [SMILES: COCC1(c2cc([Si](C)(C)C)c(O)cc2NC(=O)c2c[nH]c3ccccc3c2=O)CCC1] | |
| 28 | 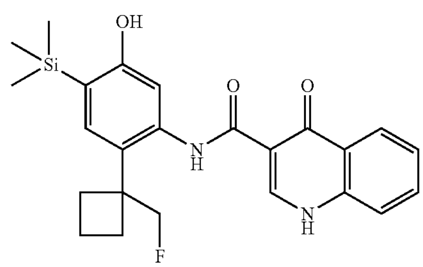 [SMILES: C[Si](C)(C)c1cc(C2(CF)CCC2)c(NC(=O)c2c[nH]c3ccccc3c2=O)cc1O] | |

While this disclosure has been particularly shown and described with references to certain embodiments thereof, it will be understood by those skilled in the art that various changes in form and details may be made therein without departing from the scope of the disclosure encompassed by the appended claims.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A compound represented by:

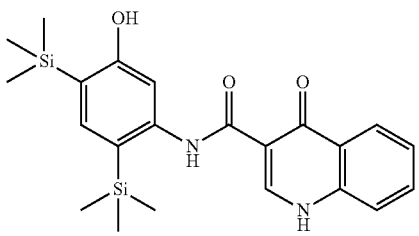

or a pharmaceutically acceptable salt thereof.

2. A pharmaceutical composition comprising the compound of claim 1 and a pharmaceutically acceptable excipient.

3. A method of enhancing cystic fibrosis transmembrane conductance regulator (CFTR) activity in a subject in need thereof comprising administering to said subject an effective amount of the compound of claim 1.

4. The method of claim 3, wherein the subject has one or more mutations in the CFTR gene, wherein the mutations are each selected from the group consisting of S549N, G551D, G1244E, G1349D, G167R, G551S, S1251N, S1255P, S549R, G178R, G970R, and R117H.

5. The method of 3, wherein the subject is suffering from a disease associated with decreased CFTR activity.

6. The method of claim 5, wherein the disease is selected from the group consisting of cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), chronic sinusitis, dry eye disease, protein C deficiency, A-β-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, Sjogren's syndrome, familial hypercholesterolemia, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, nephrogenic DI, Charcot-Marie Tooth syndrome, Perlizaeus-Merzbacher disease, Alzheimer's disease, Parkinson's disease, amyotrophic lateral sclerosis, progressive supranuclear palsy, Pick's disease, Huntington's disease, spinocerebellar ataxia type I, spinal and bulbar muscular atrophy, dentatorubral pallidoluysian, myotonic dystrophy, hereditary Creutzfeldt-Jakob disease (due to prion protein processing defect), Fabry disease, cholestatic liver disease, and Straussler-Scheinker syndrome.

7. The method of claim 6, wherein the disease is cystic fibrosis.

8. The method of claim 6, wherein the subject is a human patient.

9. The method of claim 6, further comprising administering at least one additional CFTR modulators to the subject.

10. The method of claim 9, wherein the at least one additional CFTR modulator is selected for each occurrence from the group consisting of VX-152, VX-440, VX-445, VX-659, VX-809 (lumacaftor), VX-661, FDL169, GLPG2851, GLPG2665, GLPG2737, and GLPG2222.

11. A method of treating cystic fibrosis in a patient in need thereof, comprising administering to the patient an effective amount of a compound represented by:

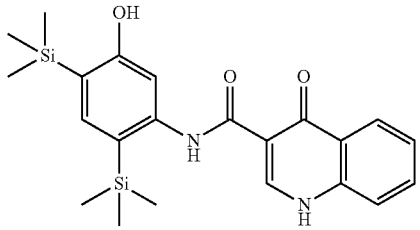

or a pharmaceutically acceptable salt thereof.

* * * * *